(12) United States Patent
Strobl

(10) Patent No.: US 10,765,442 B2
(45) Date of Patent: Sep. 8, 2020

(54) SURGICAL DEVICES AND METHODS FOR BIASING AN END EFFECTOR TO A CLOSED CONFIGURATION

(71) Applicant: Ethicon LLC, Guaynabo, PR (US)

(72) Inventor: Geoffrey S. Strobl, Williamsburg, OH (US)

(73) Assignee: Ethicon LLC, Guaynabo, PR (US)

( * ) Notice: Subject to any disclaimer, the term of this patent is extended or adjusted under 35 U.S.C. 154(b) by 434 days.

(21) Appl. No.: 15/487,787

(22) Filed: Apr. 14, 2017

(65) Prior Publication Data

US 2018/0296213 A1 Oct. 18, 2018

(51) Int. Cl.
*A61B 17/29* (2006.01)
*A61B 18/14* (2006.01)
(Continued)

(52) U.S. Cl.
CPC .......... *A61B 17/29* (2013.01); *A61B 18/1442* (2013.01); *A61B 90/03* (2016.02);
(Continued)

(58) Field of Classification Search
CPC .... A61B 17/07207; A61B 2017/00017; A61B 2017/07278; A61B 17/29; A61B 18/1442; A61B 2017/2915; A61B 2017/292; A61B 2017/2941; A61B 2017/07214; A61B 90/03; A61B 2017/07285;
(Continued)

(56) References Cited

U.S. PATENT DOCUMENTS 3,612,597 A * 10/1971 Wirkkala .................. B66C 3/12
294/112
3,654,755 A * 4/1972 Bell ........................ B25B 7/123
57/23

(Continued)

FOREIGN PATENT DOCUMENTS

WO WO-2014151621 A1 9/2014
WO WO-2014151952 A1 9/2014

OTHER PUBLICATIONS

U.S. Appl. No. 15/200,283, entitled "Methods, Systems, and Devices for Initializing a Surgical Tool," filed Jul. 1, 2016.

(Continued)

*Primary Examiner* — Robert F Long
(74) *Attorney, Agent, or Firm* — Mintz Levin Cohn Ferris Glovsky and Popeo, P.C.

(57) ABSTRACT

Surgical devices and methods are provided that utilize an end effector biased to a closed position when an actuator of the device is biased in an uncompressed configuration. End effectors according to the present disclosure can include first and second jaws that can be moved from the biased closed position to an open position by compressing the actuator from the uncompressed configuration and towards a compressed configuration. Various force assemblies and related components are provided that allow the device to achieve two end effector actuation profiles: (1) moving from a closed position and to an open position; and (2) moving from a closed position, to an open position, and back to the closed position. Various structures and methods for operating such devices during a surgical procedure are also provided.

2 Claims, 8 Drawing Sheets

(51) Int. Cl.
*A61B 17/00* (2006.01)
*A61B 17/072* (2006.01)
*A61B 90/00* (2016.01)

(52) U.S. Cl.
CPC .............. *A61B 2017/00017* (2013.01); *A61B 2017/00398* (2013.01); *A61B 2017/07214* (2013.01); *A61B 2017/07285* (2013.01); *A61B 2017/292* (2013.01); *A61B 2017/2915* (2013.01); *A61B 2017/2919* (2013.01); *A61B 2017/2934* (2013.01); *A61B 2017/2936* (2013.01); *A61B 2017/2941* (2013.01)

(58) Field of Classification Search
CPC .. A61B 2017/00398; A61B 2017/2919; A61B 2017/2936; A61B 2017/2934; A61B 2018/1455; A61B 18/1455
USPC ............................................ 227/175.1–182.1
See application file for complete search history.

(56) References Cited

U.S. PATENT DOCUMENTS

| | | | | |
|---|---|---|---|---|
| 3,922,782 | A * | 12/1975 | Lind | A01G 3/033 30/228 |
| 4,047,654 | A * | 9/1977 | Alvarado | A61B 17/115 227/19 |
| 4,312,363 | A * | 1/1982 | Rothfuss | A61B 5/1075 600/587 |
| 4,712,545 | A * | 12/1987 | Honkanen | A61B 17/1608 600/564 |
| 4,754,909 | A * | 7/1988 | Barker | A61B 17/072 227/19 |
| 5,143,414 | A * | 9/1992 | Rosellini | A61M 5/3213 128/919 |
| 5,312,023 | A * | 5/1994 | Green | A61B 17/07207 227/175.1 |
| 5,361,583 | A * | 11/1994 | Huitema | A61B 17/00 60/413 |
| 5,374,277 | A * | 12/1994 | Hassler | A61B 17/29 606/170 |
| 5,389,098 | A * | 2/1995 | Tsuruta | A61B 17/00234 606/41 |
| 5,397,325 | A * | 3/1995 | Della Badia | A61B 17/0469 112/169 |
| 5,571,090 | A * | 11/1996 | Sherts | A61B 17/0469 606/139 |
| 5,697,542 | A * | 12/1997 | Knodel | A61B 17/07207 227/175.1 |
| 5,901,895 | A * | 5/1999 | Heaton | A61B 17/07207 227/176.1 |
| 5,984,932 | A * | 11/1999 | Yoon | A61B 17/0469 606/147 |
| 6,099,537 | A * | 8/2000 | Sugai | A61B 17/0684 606/143 |
| 6,238,414 | B1 * | 5/2001 | Griffiths | A61B 17/29 606/205 |
| 7,278,563 | B1 * | 10/2007 | Green | A61B 17/07207 227/176.1 |
| 7,918,848 | B2 * | 4/2011 | Lau | A61B 17/29 606/29 |
| 8,029,035 | B1 * | 10/2011 | Bottner | B25J 1/04 294/104 |
| 8,091,753 | B2 * | 1/2012 | Viola | A61B 17/07207 227/175.1 |
| 8,535,311 | B2 * | 9/2013 | Schall | A61B 18/1445 606/51 |
| 8,764,769 | B1 * | 7/2014 | Rodriguez-Navarro | A61B 17/0218 606/142 |
| 9,113,862 | B2 * | 8/2015 | Morgan | A61B 90/92 |
| 9,161,807 | B2 * | 10/2015 | Garrison | A61B 17/29 |
| 9,386,985 | B2 * | 7/2016 | Koch, Jr. | A61B 17/07207 |
| 9,788,835 | B2 * | 10/2017 | Morgan | A61B 17/0644 |
| 10,265,073 | B2 * | 4/2019 | Scheib | A61B 17/068 |
| 2002/0076672 | A1 * | 6/2002 | Enoch | A61C 7/02 433/145 |
| 2004/0193212 | A1 * | 9/2004 | Taniguchi | A61B 17/29 606/205 |
| 2004/0232197 | A1 | 11/2004 | Shelton et al. | |
| 2005/0033278 | A1 * | 2/2005 | McClurken | A61B 18/14 606/41 |
| 2006/0053563 | A1 * | 3/2006 | Skinner | B25B 7/10 7/127 |
| 2006/0151567 | A1 * | 7/2006 | Roy | A61B 17/07207 227/175.1 |
| 2006/0151568 | A1 * | 7/2006 | Weller | A61B 17/0218 227/175.1 |
| 2007/0084896 | A1 * | 4/2007 | Doll | A61B 17/07207 227/175.2 |
| 2007/0114261 | A1 * | 5/2007 | Ortiz | A61B 17/064 227/175.1 |
| 2008/0105730 | A1 * | 5/2008 | Racenet | A61B 17/068 227/176.1 |
| 2008/0167680 | A1 * | 7/2008 | Voegele | A61B 17/00491 606/206 |
| 2008/0169327 | A1 * | 7/2008 | Shelton | A61B 17/105 227/176.1 |
| 2008/0169328 | A1 * | 7/2008 | Shelton | A61B 17/072 227/176.1 |
| 2008/0216862 | A1 * | 9/2008 | Silva | A45D 8/20 132/277 |
| 2008/0237297 | A1 * | 10/2008 | Demmy | A61B 17/07207 227/176.1 |
| 2008/0244880 | A1 * | 10/2008 | Rankin | D06F 55/02 24/500 |
| 2009/0250501 | A1 * | 10/2009 | Sonnenschein | A61B 17/0057 227/176.1 |
| 2009/0293577 | A1 * | 12/2009 | Hamm | B25B 7/02 72/416 |
| 2009/0318830 | A1 * | 12/2009 | George | A61B 10/0291 600/564 |
| 2010/0076459 | A1 * | 3/2010 | Farascioni | A61B 17/07207 606/143 |
| 2010/0148756 | A1 * | 6/2010 | Shah | G01R 1/22 324/126 |
| 2010/0213240 | A1 * | 8/2010 | Kostrzewski | A61B 17/072 227/180.1 |
| 2012/0080332 | A1 * | 4/2012 | Shelton, IV | A61B 90/92 206/339 |
| 2012/0080485 | A1 * | 4/2012 | Woodard, Jr. | A61B 90/92 227/176.1 |
| 2012/0083783 | A1 | 4/2012 | Davison et al. | |
| 2012/0116379 | A1 * | 5/2012 | Yates | A61B 17/00234 606/33 |
| 2012/0149990 | A1 * | 6/2012 | Buehler | A61B 17/0206 600/210 |
| 2013/0023868 | A1 * | 1/2013 | Worrell | A61B 17/07207 606/33 |
| 2013/0030428 | A1 * | 1/2013 | Worrell | A61B 5/0205 606/33 |
| 2013/0158593 | A1 * | 6/2013 | Kiapour | A61B 17/29 606/205 |
| 2013/0161374 | A1 | 6/2013 | Swayze et al. | |
| 2014/0027491 | A1 * | 1/2014 | Beardsley | A61B 17/07207 227/175.1 |
| 2014/0039470 | A1 * | 2/2014 | Mueller | A61B 17/00 606/1 |
| 2014/0069982 | A1 * | 3/2014 | Zhao | B25C 5/06 227/132 |
| 2014/0151428 | A1 * | 6/2014 | Boudreaux | A61B 18/1445 227/175.1 |
| 2015/0173755 | A1 * | 6/2015 | Baxter, III | A61B 17/072 227/180.1 |
| 2015/0173756 | A1 * | 6/2015 | Baxter, III | A61B 17/07207 227/177.1 |
| 2015/0190191 | A1 | 7/2015 | Strobl | |
| 2015/0209059 | A1 * | 7/2015 | Trees | A61B 18/1445 606/170 |

(56) References Cited

U.S. PATENT DOCUMENTS

| | | | |
|---|---|---|---|
| 2016/0000041 A1* | 1/2016 | Ricker | A47G 25/80 |
| | | | 119/850 |
| 2016/0058439 A1* | 3/2016 | Shelton, IV | A61B 17/068 |
| | | | 227/176.1 |
| 2016/0262756 A1* | 9/2016 | Patankar | A61B 17/07207 |
| 2016/0374678 A1* | 12/2016 | Becerra | A61B 17/07207 |
| | | | 227/177.1 |
| 2017/0105725 A1* | 4/2017 | Scheib | A61B 17/07207 |
| 2017/0105729 A1* | 4/2017 | Scheib | A61B 17/068 |
| 2017/0105733 A1* | 4/2017 | Scheib | A61B 17/068 |
| 2017/0119402 A1* | 5/2017 | Heinemann | A61B 17/1608 |
| 2017/0135712 A1* | 5/2017 | Boudreaux | A61B 18/1445 |
| 2017/0224343 A1* | 8/2017 | Baxter, III | A61B 17/32 |
| 2017/0367752 A1* | 12/2017 | Boudreaux | A61B 18/1445 |
| 2018/0092703 A1* | 4/2018 | Rodriguez-Navarro | |
| | | | A61B 17/29 |
| 2018/0168636 A1* | 6/2018 | Shelton, IV | A61B 17/07207 |
| 2018/0168641 A1* | 6/2018 | Harris | A61B 17/29 |
| 2018/0296213 A1* | 10/2018 | Strobl | A61B 17/29 |
| 2019/0046192 A1* | 2/2019 | Dunki-Jacobs | A61B 17/072 |
| 2019/0183503 A1* | 6/2019 | Shelton, IV | A61B 17/07207 |
| 2020/0060676 A1* | 2/2020 | Gettinger | A61B 17/07207 |

OTHER PUBLICATIONS

U.S. Appl. No. 15/237,653 entitled "Methods, Systems, and Devices for Controlling a Motor of a Robotic Surgical System" filed Aug. 16, 2016.

* cited by examiner

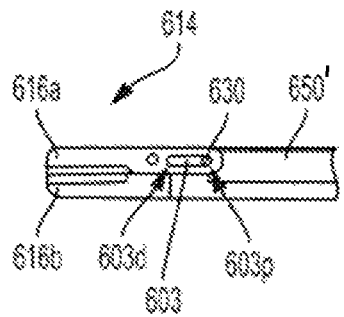
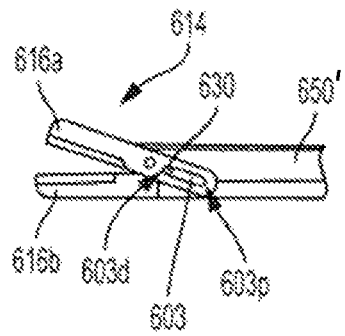
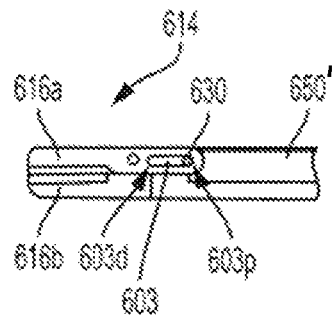
FIG. 10A  FIG. 10B  FIG. 10C
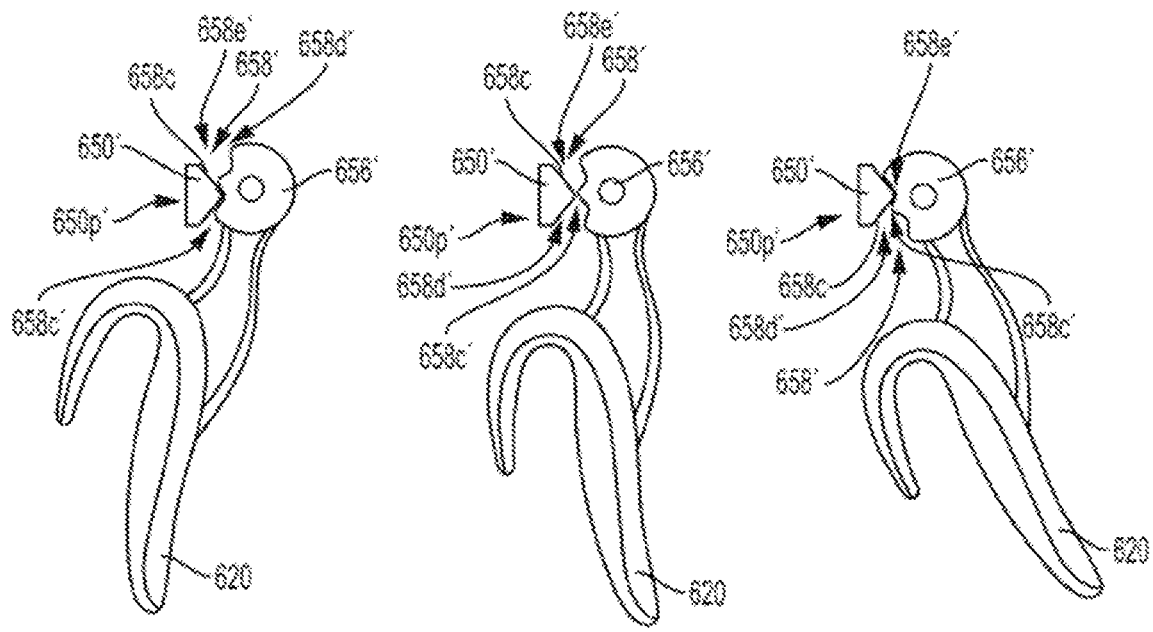
FIG. 11A  FIG. 11B  FIG. 11C

SURGICAL DEVICES AND METHODS FOR BIASING AN END EFFECTOR TO A CLOSED CONFIGURATION

FIELD

The present disclosure relates to surgical devices and methods for grasping tissue, and more particularly relates to devices and methods that include end effectors for grasping tissue that are biased to a closed configuration.

BACKGROUND

Surgical devices are used in various open, endoscopic, and laparoscopic surgeries to manipulate tissue, staple tissue, and/or transect tissue volumes and blood vessels. These devices can include jaws for grasping tissue therebetween and, optionally, a cutting mechanism that can be advanced through the grasped tissue to transect it. The cutting mechanism can be designed to travel within a track formed in one or both jaws. In some instances the devices can also be used to seal tissue volumes and blood vessels being transected, for instance by applying electrical energy to the grasped tissue to seal it before tissue transection is completed. For example, various mono-polar and bi-polar radio frequency (RF) surgical instruments and surgical techniques have been developed for sealing tissue volumes and blood vessels. Electrodes can be disposed on a face of one or both of the jaws and can apply energy to the grasped tissue to promote hemostasis.

Many surgical devices configured to grasp tissue are configured such that squeezing a closure actuator causes jaws of a jaw assembly to close. Many different mechanical and/or electrical set-ups can allow for this set-up to be effective. For example, some surgical devices incorporate mechanical linkages between a closure actuator and jaws, and when a user manipulates the closure actuator by manually squeezing a trigger or lever arm, the jaws of the end effector can move from an open position to a closed position. In such configurations, however, high manual forces may be necessary for a user to operate the closure actuator, especially in a mechanically-actuated device. This can be problematic during a surgical procedure because a user may experience hand fatigue from repeatedly squeezing the closure actuator and/or having to hold the closure actuator adjacent to the stationary portion of the handle so that the jaws are in a closed position and compress tissue with the desired force. There is also a limit as to the amount of tissue compression that a user can achieve by manually squeezing a closure actuator. Still further, because devices having jaws inserted to a surgical site are generally held in a closed configuration to decrease the size of the profile of the device as it navigates through the body, a user often has to exert enough force on the closure actuator to hold the jaws in the closed position while navigating through the body.

Accordingly, there is a need for surgical devices and methods that can reduce the force required to actuate the device and/or reduce a user's hand fatigue during use.

SUMMARY

In general, surgical devices and methods for biasing an end effector to a closed configuration are provided.

A surgical device is provided that in one embodiment includes a housing having a stationary portion, an elongate shaft extending distally from the housing, and an end effector coupled to a distal end of the elongate shaft, configured to engage tissue, and configured to move between a closed position and an open position. The surgical device also includes a closure actuator configured to be actuated to move with respect to the stationary portion. The closure actuator is biased away from the stationary portion in an uncompressed configuration such that the end effector is in the closed position, and the closure actuator is configured to move against the bias towards the stationary portion and thereby cause the end effector to move from the closed position towards the open position.

The surgical device can have any number of variations. For example, the closure actuator can be at a maximum distance away from the stationary portion in the uncompressed configuration, the closure actuator moving against the bias towards the stationary portion can move the closure actuator from the uncompressed configuration to a compressed configuration in which the closure actuator is at a minimum distance away from the stationary portion, and the end effector can be in the open position when the closure actuator is in the compressed configuration. In at least some embodiments, the closure actuator can be configured to move from the compressed configuration back to the uncompressed configuration, thereby causing the end effector to move from the open position back to the closed position.

For another example, the closure actuator can be at a maximum distance away from the stationary portion in the uncompressed configuration, the closure actuator moving against the bias towards the stationary portion can move the closure actuator from the uncompressed configuration to a compressed configuration in which the closure actuator is at a minimum distance away from the stationary portion, and the end effector can be in the closed position when the closure actuator is in the compressed configuration. In at least some embodiments, when the closure mechanism is at a distance away from the stationary portion that is between the minimum and maximum distances, the end effector can be in the open position. In at least some embodiments, the closure actuator can be configured to move from the compressed configuration back to the uncompressed configuration, thereby causing the end effector to move from the closed position to the open position and then back to the closed position.

For yet another example, the surgical device can include a force-translating component operatively coupled to the closure actuator and can be disposed in a slot formed in the end effector, and the actuation of the closure actuator can be configured to cause the force-translating component to slide within the slot and thereby cause the end effector to move from the closed position towards the open position. In at least some embodiments, the force-translating component includes an elongate rod extending along the shaft and having a distal protrusion that is configured to slide within the slot.

For still another example, the surgical device can include a cam operatively coupled to the closure actuator and slidably engaged with a cam surface formed on the end effector, and the actuation of the closure actuator can be configured to cause the cam to slide along the cam surface and thereby cause the end effector to move from the closed position towards the open position. For another example, the surgical device can include an elongate rod having a distal end disposed within the housing and having an elongate portion extending along the shaft, and the actuation of the closure actuator can be configured to push the rod distally and thereby cause the end effector to move from the closed position towards the open position. For yet another example, the movement of the closure actuator against the bias towards the stationary portion can move the closure actuator to a semi-compressed configuration in which the end effector is in the open position, and further movement of the closure actuator against the bias and towards the stationary portion to a compressed configuration can cause the end effector to return to the closed position. For still another example, the closure actuator can include a movable trigger. For another example, the end effector can include a pair of opposed jaws configured to engage the tissue therebetween.

In another embodiment, a surgical device includes an elongate shaft having at a distal end thereof an end effector configured to engage tissue and to move between open and closed positions. The end effector is biased to the closed position. The surgical device also includes an elongate rod extending along the shaft and operatively coupled to the end effector, and an actuator operatively coupled to the rod and configured to be actuated to move from a first position, in which the end effector is in the closed position, to a second position and thereby cause the rod to move distally. The distal movement of the rod is configured to cause the end effector to move from the closed position towards the open position.

The surgical device can vary in any number of ways. For example, the actuator can be configured to move from the second position to a third position and thereby continue moving the rod distally, and the continued distal movement of the rod can be configured to cause the end effector to move from the open position back to the closed position. For another example, the actuator can be fully actuated in the second position, the actuator can be configured to move from the second position back to the first position and thereby cause the rod to move proximally, and the proximal movement of the rod can be configured to cause the end effector to move from the open position back to the closed position. For yet another example, the closure actuator can include a movable trigger, and the end effector can include a pair of opposed jaws configured to engage the tissue therebetween.

The force-translating component can have a variety of configuration and is encompassed by a variety of structures both disclosed in the present application and known to those skilled in the art. The component, can be, for example, a compression member, an I-beam or I-blade, a rod, a shaft, or any other elongate structure capable of translating movement from the force assembly disposed in the housing to operate the end effector. In some embodiments the force-translating component is a compression member that is slidably disposed within the longitudinal bore of the shaft. The compression member can include one or more force-applying surfaces (e.g., flanges of an I-beam or I-blade) at a distal end of the compression member, with the force-applying surface(s) being configured to apply a force to at least one of the jaws to move the jaws from the closed position to the open position. In another aspect, a method for operating a surgical device is provided that in one embodiment includes inserting an end effector of a surgical device into a body to a surgical site with first and second jaws of the end effector being in a biased closed position and an actuator at a proximal portion of the surgical device being in an uncompressed configuration. The method also includes moving the actuator from the uncompressed configuration towards a compressed configuration such that the first and second jaws are in an open position.

The method can vary in any number of ways. For example, the method can include, after moving the actuator from the uncompressed configuration towards the compressed configuration, moving the actuator to the compressed configuration and thereby move the first and second jaws back to the closed position. For another example, moving the actuator from the uncompressed configuration towards the compressed configuration can include moving the actuator to the compressed configuration such that the first and second jaws are in the open position.

BRIEF DESCRIPTION OF DRAWINGS

This disclosure will be more fully understood from the following detailed description taken in conjunction with the accompanying drawings, in which:

FIG. 10A is a schematic side view of still another exemplary embodiment of an end effector, the end effector being in a first, closed position;

FIG. 10B is a schematic side view of the end effector of FIG. 10A, the end effector being in a second, open position;

FIG. 10C is a schematic side view of the end effector of FIG. 10A, the end effector being in a third, closed position;

FIG. 11A is a schematic side view of one exemplary embodiment of a closure actuator and an internal cam mechanism of a surgical device having an end effector, the closure actuator being in a first, uncompressed configuration with respect to the internal cam mechanism and a stationary arm (not shown) of the surgical device with the end effector being in a first, closed position;

FIG. 11B is a schematic side view of the closure actuator and internal cam mechanism of FIG. 11A, the embodiment illustrating the closure actuator being in a second, semi-compressed configuration with respect to the internal cam mechanism and the stationary arm (not shown) with the end effector being in a second, open position;

FIG. 11C is a schematic side view of the closure actuator and internal cam mechanism of FIG. 11B, the embodiment illustrating a third, compressed configuration of the closure actuator with respect to the internal mechanism and the stationary arm (not shown) when the end effector is a in a third, closed position;

DETAILED DESCRIPTION

Figure 1:
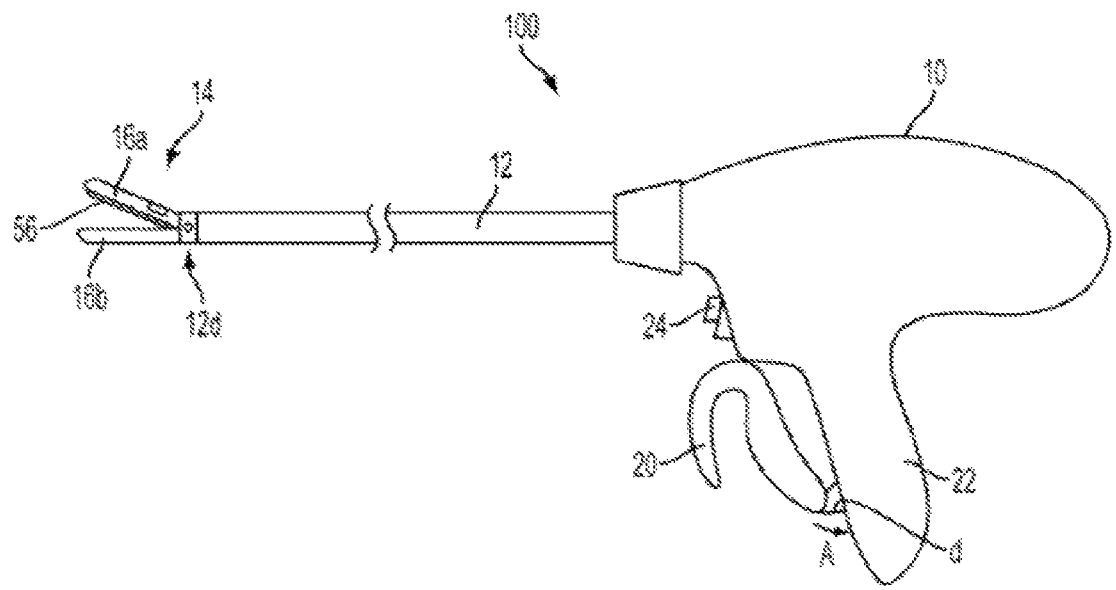
FIG. 1 is a schematic side view of one exemplary embodiment of a surgical device having an end effector and a housing with an actuator and an stationary arm, the actuator being in a compressed configuration in which the actuator is adjacent to the stationary arm and the end effector being in an open position.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present application. Further, to the extent features, sides, or steps are described as being "first" or "second," such numerical ordering is generally arbitrary, and thus such numbering can be interchangeable. Further, in the present disclosure, like-numbered components and like-named components of the various embodiments generally have similar features when those components are of a similar nature and/or serve a similar purpose.

Additionally, the figures are not necessarily to scale and, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can be determined for any geometric shape. Still further, sizes and shapes of the devices, and the components thereof, can depend at least on the anatomy of the subject in which the instruments will be used, the size and shape of components with which the devices will be used, and the methods and procedures in which the devices will be used.

Surgical devices and methods are provided for operating a surgical device having an end effector that is configured to be biased into a closed position. In general, a surgical device having an end effector can have two end effector actuation profiles: (1) a first actuation profile in which the end effector is in a closed position and moves to an open position; and (2) a second actuation profile in which the end effector is in a closed position, moves to an open position, and then returns to a closed position. Variants of the open and closed positions can also be provided, e.g., partially open or partially closed. An actuator of the surgical device configured to be actuated to operate the end effector can be configured to move between multiple positions or configurations, including uncompressed positions or configurations (also referred to herein as open positions or configurations), compressed positions or configurations (also referred to herein as closed positions or configurations), and variants thereof, such as semi-compressed positions or configurations (also referred to herein as semi-open or semi-closed positions or configurations). In an exemplary embodiment, when the actuator is biased in a first, uncompressed (open) configuration, it can be configured to cause the end effector to be in a closed position. The end effector can thus be biased to a closed position such that the surgical device, when not in operation, can default to a configuration in which the end effector is closed. The actuator can then be advanced towards a closed position, such as by squeezing, pulling, or compressing the actuator towards a stationary handle of the surgical device (either manually or by a robotic surgical system, electronic system, or other controlled system) to effect movement in the end effector to move it to the open position. In some embodiments, the open position of the end effector may be achieved once the actuator is in the fully compressed configuration in which the actuator is adjacent to the stationary handle. In other embodiments, the open position of the end effector may be achieved when the actuator is in a semi-compressed configuration that is between the uncompressed and compressed configurations, and upon the end effector achieving the open position, further advancement of the actuator towards the stationary handle can advance the end effector back to the closed position. A person skilled in the art will appreciate that the open position of the end effector may be a fully open position, or it may be a partially open position.

Figure 2:
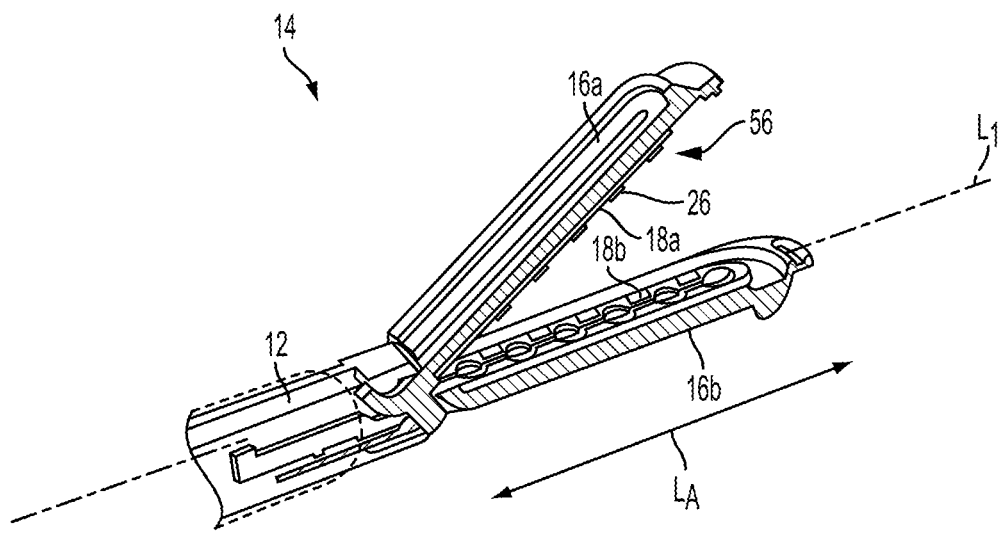
FIG. 2 is a perspective partial cross-sectional view of the end effector of FIG. 1 in the open position.
Figure 3:
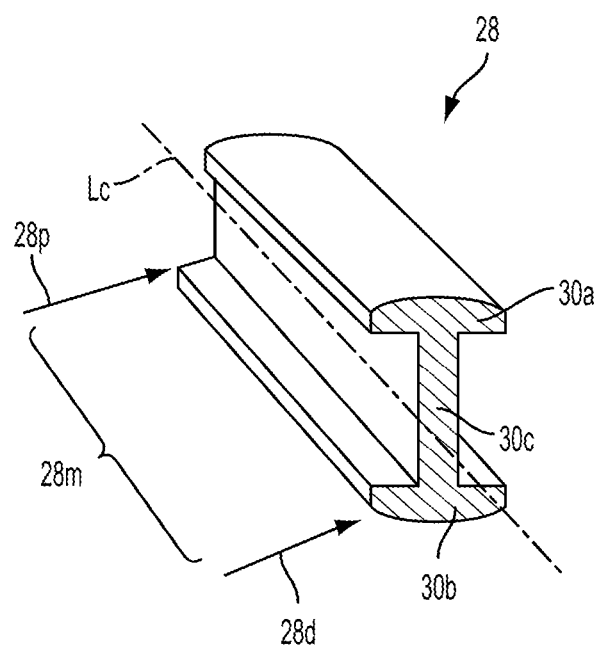
FIG. 3 is a perspective view of a compression member of the surgical device of FIG. 1.

FIGS. 1-3 illustrate one exemplary embodiment of a surgical device 100 configured to control the movement of an end effector 14 disposed at a distal end 12d of a shaft portion 12 (also referred to herein as a shaft). The shaft portion 12 extends distally from a housing or proximal handle portion 10 of the surgical device 100. The shaft portion 12 can be removably and replaceably attached to the housing 10 or components therein in manners that are known to those skilled in the art. In other embodiments, the shaft portion 12 can be integrally formed with respect to the housing 10.

Figure 1A:
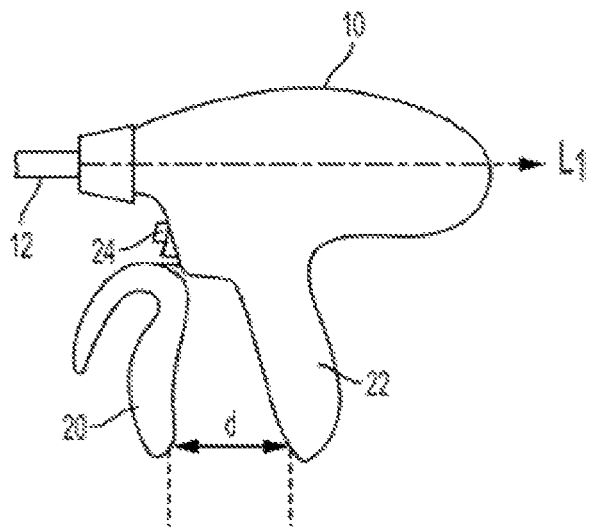
FIG. 1A is a schematic side view of a proximal portion of the surgical device of FIG. 1 with the actuator in an uncompressed configuration.

The housing 10 can be any type of pistol-grip or other type of handle known in the art that is configured to carry and/or engage various components used in conjunction with actuating the end effector 14, such as motors, controllers, levers, triggers, sliders, and/or other components, and/or with performing other surgical functions or movements of the device 100. The housing 10 includes a closure actuator 20 and includes a stationary arm 22, also referred to herein as a stationary handle. The closure actuator 20 is biased to an uncompressed or open configuration, which is shown in FIG. 1A. Various components and embodiments for achieving that configuration are described in greater detail below. A person skilled in the art will appreciate that while the term "handle" can be used in conjunction with the stationary arm 22, in some embodiments, such as those that involve actuation of the closure actuator by a robotic surgical system, electronic system, or other controlled system and thus do not involve manual actuation of the closure actuator, the stationary arm 22 does not have to be "handled" by hand Thus, the stationary arm 22 can serve as a reference point to describe the location of the actuator 20, and does not have to be "handled" by hand.

In some embodiments, the housing 10 can be configured for use with a robotic surgery platform, as opposed to a user's hand. In such embodiments, the closure actuator 20 can have a different configuration than shown in the embodiment of FIGS. 1-3, such as by being included as part of a tool housing configured to be operatively coupled to the robotic surgery platform to allow the robotic surgery platform to provide inputs to the tool housing to selectively open and close the end effector 14, e.g., to provide an input to the tool housing to cause linear movement of a rod or other force-translating component of the surgical device. Various embodiments of tool housings of surgical instruments configured to be operatively coupled to a robotic surgery platform are further described in International Pat. Pub. No. WO 2014/151952, entitled "Compact Robotic Wrist," filed Mar. 13, 2014; International Pat. Pub. No. WO 2014/151621, entitled "Hyperdexterous Surgical System," filed Mar. 13, 2014; U.S. patent application Ser. No. 15/200,283, entitled "Methods, Systems, And Devices For Initializing A Surgical Tool," filed Jul. 1, 2016; and in U.S. patent application Ser. No. 15/237,653 entitled "Methods, Systems, And Devices For Controlling A Motor Of A Robotic Surgical System" filed Aug. 16, 2016; the entire contents of which are hereby incorporated by reference.

Referring again to FIGS. 1-3, movement of the closure actuator 20 towards and away from the stationary arm 22 in a direction A, or between uncompressed (open) and compressed (closed) configurations or positions, can be configured to control the movement of the end effector 14. More particularly, as shown, the end effector 14 includes jaws 16a, 16b, which can be opened and closed by moving the actuator 20 with respect to the stationary arm 22. As described further below, the jaws 16a, 16b can be configured to grasp tissue, and then additional surgical functions can be performed on the grasped tissue using the device 100 and/or other surgical tools, such as cutting or transecting and/or sealing the tissue. While the illustrated end effector 20 has a pair of opposed jaws 16a, 16b, other types, size, shapes, and configurations of end effectors can be used as an end effector in the surgical devices described herein without departing from the spirit of the present disclosure. As shown in FIG. 1, a distance d exists between the closure actuator 20 and the stationary arm 22 when the closure actuator 20 is in the closed configuration. The distance d is greater when the closure actuator 20 is in the uncompressed configuration than when the closure actuator 20 is in the compressed configuration. Likewise, the distance d when the closure actuator 20 is in the semi-compressed configuration is greater than the distance d when the closure actuator 20 is in the compressed configuration and is less than the distance d when the closure actuator 20 is in the uncompressed configuration. FIG. 1 shows the closure actuator 20 in the compressed configuration, and FIG. 1A shows the closure actuator 20 in the uncompressed configuration. In general, the actuator 20 is in the closed configuration when the actuator 20 is at a minimum possible distance d from the stationary handle 22 and is in the open configuration when the actuator 20 is at a maximum possible distance d from the stationary handle 22. The distance d is non-zero in this illustrated embodiment when the actuator 20 is in the closed configuration, but in other embodiments, the distance d is substantially zero when the actuator 20 is in the closed configuration. A person skilled in the art will appreciate that the distance d may not be precisely zero but nevertheless considered to be substantially zero due to any one or more factors, such as manufacturing tolerances and sensitivity of measurement devices. A distance between the jaws 16a, 16b is greater when the jaws 16a, 16b are in an open position than when the jaws 16a, 16b are in a closed position. The distance between the jaws 16a, 16b increases as the jaws 16a, 16b move from the closed configuration to and the open configuration, and similarly decreases when the jaws 16a, 16b move from the open configuration to the closed configuration.

The shaft portion 12 can include a bore (not shown) extending longitudinally along axis $L_1$ through the shaft portion 12 and configured to contain therein one or more mechanisms, such as a rod, inner shaft, and/or compression member, for actuating the end effector 14.

Figure 4:
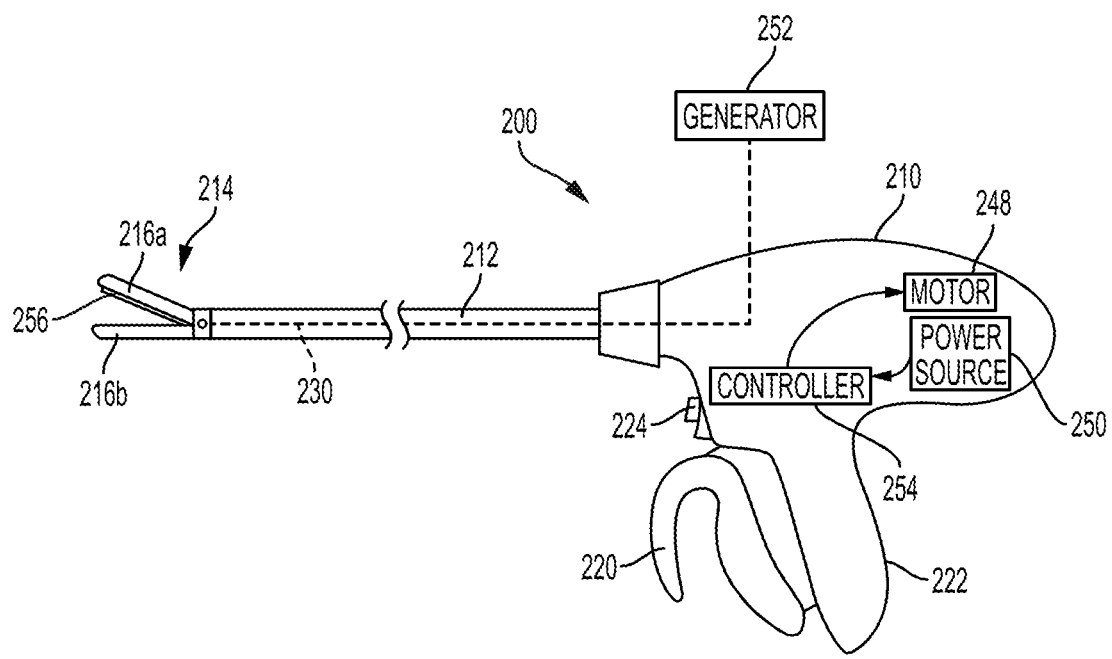
FIG. 4 is a schematic side view of another exemplary embodiment of a surgical device, the device having an end effector and a housing with an actuator and a stationary arm, the actuator being in a compressed configuration in which the actuator is adjacent to the stationary arm and the end effector being in an open position.
Figure 7A:
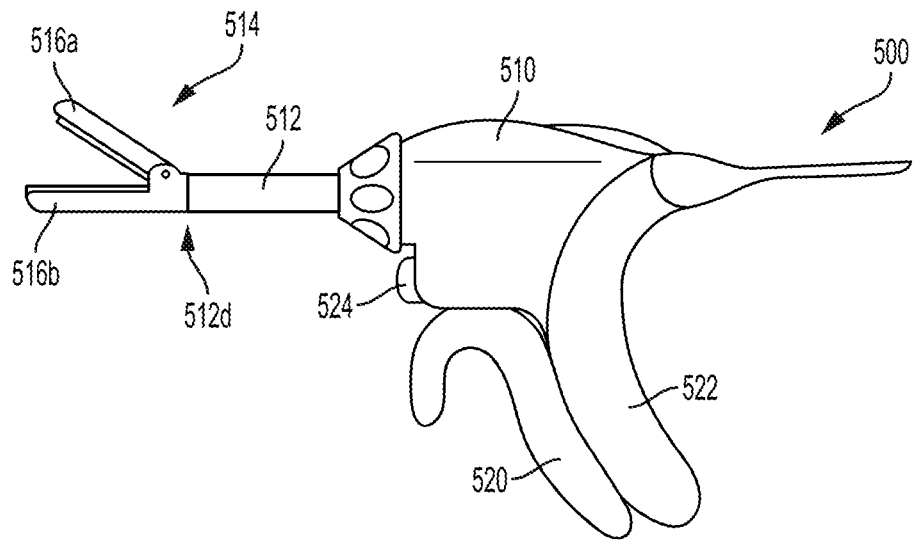
FIG. 7A is a schematic side view of yet another exemplary embodiment of a surgical device, the device having an end effector and a housing with an actuator and a stationary arm, the actuator being in a compressed configuration in which the actuator is adjacent to the stationary arm and the end effector being in an open position.

As in this illustrated embodiment, the surgical device 100 can include a firing actuator 24 configured to deliver energy to tissue grasped by the jaws 16a, 16b. Actuation of the firing actuator 24 can be configured to complete a circuit to power one or more electrodes associated with the jaws 16a, 16b (such as electrodes on tissue-engaging surfaces 18a, 18b of one or both of the jaws 16a, 16b) to seal tissue between the jaws 16a, 16b. More particularly, completion of the circuit by actuating the firing actuator 24 can allow electrical energy to pass from a power source (not shown), through one or more electrical leads (not shown), and to an electrode 56 disposed on the upper jaw 16a for contacting and sealing tissue. The lower jaw 16b does not have an associated electrode in this illustrated embodiment but can have such an electrode in other embodiments in addition to or instead of the upper jaw 16a having an electrode, such as the electrode 56, associated therewith. The electrical lead(s) can be disposed in the shaft portion 12 to electrically connect the firing actuator 24 and the electrode 56. The power source can be provided in the housing 10, such as shown in the embodiment of FIG. 4, or the power source can be external of the housing 10 and the housing 10 can be configured to electrically connect to the power source, for instance by way of a socket extending from the housing 10 to connect to the power source, such as illustrated in the embodiment of FIG. 7A, by using a cord extending from the housing 10, or by using another connection. The firing actuator 24 is in the form of a button in this embodiment but can have other configurations. The firing actuator 24 can be configured to effect a function of the end effector 14 in addition to or instead of applying energy By way of non-limiting example, the firing actuator 24 can be configured to be actuated to operate a cutting member to fire and cut tissue grasped between the jaws 16a, 16b, such as a knife, blade, or other cutting member that is separate from any compression member 28 and/or other component(s) used to open/close the jaws 16a, 16b.

The end effector 14 includes the first, upper jaw 16a and the second, lower jaw 16b, one or both of which can be configured to move or approximate about an axis. Both of the jaws 16a, 16b can be movable relative to the shaft portion 12 or, alternatively, a single one of the jaws 16a, 16b can be configured to pivot so that the end effector 14 can move between closed and open positions. When the jaws 16a, 16b are in the closed position, a longitudinal axis of the upper jaw 16a can be substantially parallel to a longitudinal axis of the lower jaw 16b and opposed tissue-engaging surfaces 18a, 18b of the jaws 16a, 16b can be in direct contact with one another when tissue is not disposed between the jaws 16a, 16b. Alternatively, the tissue-engaging surfaces 18a, 18b of the jaws 16a, 16b can be spaced a small distance apart from one another when the jaws 16a, 16b are in the closed position, which can facilitate tissue disposed between the jaws 16a, 16b being adequately held by the jaws 16a, 16b when the jaws 16a, 16b are in the closed position. In the embodiment illustrated in FIG. 1, the upper jaw 16a is configured to pivot relative to the shaft portion 12 and relative to the lower jaw 16b while the lower jaw 16b remains stationary. In other embodiments, the lower jaw 16b can be configured to move with respect to a stationary upper jaw 16a, or both jaws 16a, 16b can be configured to pivot with respect to each other.

The end effector 14 in illustrated in FIGS. 1-2 in an open position. The jaws 16a, 16b each have a substantially elongate and straight shape, but one or both of the jaws 16a, 16b can be, for example, curved along axis $L_1$. The jaws 16a, 16b can have any suitable axial length $L_A$ for engaging tissue, where the axial length $L_A$ is measured along a longitudinal axis $L_1$ of the end effector 14, as shown in FIG. 2. The axial length $L_A$ of the jaws 16a, 16b can also be selected, at least in part, based on the targeted anatomical structure for transection and/or sealing, and the size, shape, and configuration of the other components of the device 100.

The electrode 56 can have a variety of sizes, shapes, and configurations. As in this illustrated embodiment, the electrode 56 can be substantially flat and complementary to a substantially flat surface 18a of the upper jaw 16a. Energy can be supplied thereto, for instance by the firing actuator 24, as described above. Other ways of energizing the electrode 56 (and other electrode(s) if more than one is provided and desired to be used, or the lower jaw's electrode if it includes the electrode instead of the upper jaw 16a) can be implemented, as will be appreciated by a person skilled in the art.

Either one or both of the jaws' tissue engagement surfaces 18a, 18b can include one or more surface features formed thereon that can help secure tissue when grasped between the jaws 16a, 16b. For example, the surface features can include various teeth, ridges, or depressions configured to increase friction between the tissue and the engagement surfaces 18a, 18b of the jaws 16a, 16b without tearing or otherwise damaging the tissue in contact with such surface features. In this illustrated embodiment, a plurality of teeth 26 are positioned along an axial length of both of the engagement surfaces 18a, 18b and can be configured to facilitate grasping tissue and forming substantially smooth, uniform layers of tissue to improve tissue effect.

The first and second jaws 16a, 16b can include features for interacting with a force-translating component, such a compression member, rod, or other structure extending through the shaft portion 12 and configured to translate movement of a force assembly (described in greater detail below) to the end effector 14 to operate the end effector 14. In the illustrated embodiment of FIG. 3, the force-translating component is a compression member 28 configured to apply compressive forces on the jaws 16a, 16b and tissue. In other embodiments, the force-translating component can be a rod (of any shape) or any other structure capable of translating movement from the housing side of the device 100 to the end effector side of the device 100. The first and second jaws 16a, 16b can include first and second recessed slots (not shown, although they can be formed right at the cross section edge illustrated in FIG. 2) that can receive portions of the compression member 28 and act as a track to direct movement of the compression member 28. As the compression member 28 is actuated distally along the axial length $L_A$ of the jaws 16a, 16b, the compression member 28 can apply a force to one or both of the jaws 16a, 16b to approximate their tissue-engaging surfaces 18a, 18b closer together. Further, in at least some embodiments, the compression member 28 can include a cutting member in the form of a cutting edge that is effective to transect tissue disposed within the jaws 16a, 16b as the compression member 28 is advanced distally. The cutting edge can be disposed on a distal most end 28d of the compression member 28, such as on a distal face of an upper flange 30a of the compression member 28, and can be configured to cut or transect tissue as the compression member 28 is advanced distally through the jaws 16a, 16b, as described further below.

A compression member can have various sizes, shapes, and configurations. In general, a compression member can have an elongate shape and can be movable proximally and distally along the longitudinal axis $L_1$ of the end effector 14. An exemplary compression member 28 is illustrated in FIG. 3. As shown, the compression member 28 can have a proximal end 28p, a medial portion 28m, and a distal end 28d. The proximal end 28p and the medial portion 28m of the compression member 28 can be sized and shaped to reciprocate within the shaft portion 12 of the device 100, while the distal end 28d of the compression member 28 can be sized and shaped to interact with the jaws 16a, 16b of the end effector 14. A longitudinal axis $L_C$ of the compression member 28 can be substantially aligned and coaxial with longitudinal axis $L_1$ of the end effector 14 and of the shaft portion 12, though other configurations are possible.

The compression member 28 can be actuatable from the proximal handle portion 10 of the instrument 100 by any suitable mechanism that is operatively coupled to the proximal end 28p of the compression member 28, such as via the closure actuator 20 shown in FIG. 1. The compression member 28 can include a connecting portion 30c and upper and lower flanges 30a, 30b, thus providing an "I-beam" type cross-sectional shape at the distal end 28d of the compression member 28. In the illustrated embodiment, the upper and lower flanges 30a, 30b are positioned substantially perpendicular to the connecting portion 30c to form the "I-beam" shape. As previously mentioned, the upper and lower flanges 30a, 30b can be sized and shaped to slide in recessed slots in each of the upper and lower jaw 16a, 16b, and this sliding contact of lateral edges of the flanges 30a, 30b and sides of each of the recessed slots can prevent lateral flexing of the jaws 16a, 16b. In other embodiments, including those described below, the distal portion of the compression member, or force-translating component more generally, that provides a force to at least one of the jaws can be one or more pins instead of flanges, and/or other structures that can be associated with a force-translating component to impart a force on at least one of the two jaws. A person skilled in the art will appreciate that a variety of configurations of a distal end of a force-translating component can be used to impart such a force on the jaw(s). Generally, components such as flanges, pins, and other force-imparting structures as described herein can be described as force-applying surfaces of the force-translating component (e.g., the compression member).

The compression member 28 can have various other configurations. For example, the upper flange 30a can have a width that is greater than a width of the lower flange 30b, the widths being measured in a direction perpendicular to the longitudinal axis $L_C$ of the compression member 28. The compression member 28 can vary in any number of ways and need not be limited to the illustrated embodiment. For example, the upper and lower flanges 30a, 30b can be disposed on or substantially on the distal end 28d of the compression member 28 and need not extend from the proximal end 28p to the distal end 28d of the compression member 28. Further, as described below, various components of the housing 10 and components associated with the end effector 14 can allow the compression member 28 to help move the end effector 14 between the two types of profiles (e.g., closed-open profile and closed-open-closed profile). Still further, the compression member 28 can be replaced more generally by a rod or inner shaft configured to advance distally to actuate the end effector 14, or the compression member 28 can be coupled to such a rod or inner shaft such that movement of the rod or inner shaft causes akin movement of the compression member 28.

In at least some embodiments, the device 100 can include a cutting member configured to transect tissue captured between the jaws 16a, 16b. The cutting member can have various sizes, shapes, and configurations. The cutting member can be sized and shaped to transect or cut various thicknesses and types of tissue positioned between the jaws 16a, 16b of the end effector 14. As mentioned above, in at least some embodiments, the cutting member can be a cutting edge positioned at the distal end 28d of the compression member 28, such as by being formed on the connecting portion 30c of the compression member 28 and/or on the upper flange 30a of the compression member 28. The cutting edge can have a sharp or serrated edge configured to transect the tissue. In at least some embodiments, the cutting edge can be recessed relative to distal ends of upper and lower flanges 30a, 30b of the compression member 28 so that compression occurs prior to transecting or cutting of the tissue. In at least some embodiments, the cutting member can be a knife blade or the like that is not attached to a compression member, such that the cutting member can advance and retract relative to the jaws 16a, 16b without applying compression to the tissue grasped by the jaws 16a, 16b.

Referring back to FIG. 1, the surgical device 100 can have a closure actuator, such as the closure actuator 20, which can be configured to open and close the jaws 16a, 16b of the end effector 14 by way of the compression member 28 (or otherwise, as discussed above). In an embodiment of the end effector 14 with a closed-open-closed profile, as the actuator 20 is compressed to move from the uncompressed configuration towards the stationary arm 22 and to the semi-compressed configuration, the compression member 28 advances distally to cause the end effector 14 to move to an open position. As the actuator 20 moves further towards the stationary arm 22 and from the semi-compressed configuration to the compressed configuration, the compression member 28 continues to advance distally to cause the end effector 14 to move back to the closed position. Thus, a single stroke or movement of the actuator 20 from the uncompressed configuration to the compressed configuration can be configured to cause the jaws 16a, 16b to open and then to move back together to grasp or clamp tissue disposed therebetween. In an embodiment of the end effector 14 with a closed-open profile, as the actuator 20 moves from the uncompressed configuration towards the stationary arm 22 and to the compressed configuration, the compression member 28 advances distally to cause the end effector 14 to move to an open position. In order to subsequently grasp tissue disposed between the jaws 16a, 16b, the actuator 20 needs to move from the compressed configuration to the uncompressed configuration, thus causing the jaws 16a, 16b to close and grasp the tissue.

The device 10 can be configured such that the end effector 14 has either the first profile or the second profile. In other words, the end effector 14 can either be configured to close and then open in response to actuation of the closure actuator 20 (first profile) and the closure actuator's accordant movement from the uncompressed configuration to the compressed configuration, or to close, then open, then be closed again in response to actuation of the closure actuator 20 (second profile) and the closure actuator's accordant movement from the uncompressed configuration to the compressed configuration.

In the first profile of the end effector 14, the jaws 16a, 16b of the end effector 14 are caused to be in the closed position when the closure actuator 20 is in the uncompressed (or open) configuration or position. The closure actuator 20 is biased to the first, uncompressed configuration, and the jaws 16a, 16b are biased accordingly in the first, closed position. When the closure actuator 20 is in the first position, from the closure actuator 20 is at a furthest distance d from the stationary arm 22. Because the jaws 16a, 16b are biased closed and the actuator 20 is biased open, the profile of the end effector 14 can be smaller (the amount of space taken up by the end effector) during insertion of the end effector 14 into a patient's body, and a user (or non-manual system such as a robotic surgical system, etc.) can advance the end effector 14 through the patient's body and to a surgical site without having to expend any energy squeezing or otherwise compressing the actuator 20 to close the jaws 16a, 16b as is typically required for surgical devices. In turn, the closure actuator 20 can be advanced towards the second, closed position in which the closure actuator 20 is moved closer to the stationary arm 22 such that the distance d decreases. When the closure actuator 20 is in the second, compressed (or closed) configuration or position, the jaws 16a, 16b of the end effector 14 are caused to be in the second, open position, such that the distance or space between the jaws 16a, 16b is larger when the jaws 16a, 16b are in the second position than when the jaws 16a, 16b are in the first position.

In the second profile of the end effector 14, the jaws 16a, 16b are caused to be in the first, closed position when the closure actuator 20 is in the first, open position. The closure actuator 20 is biased to the first, open position, with the jaws 16a, 16b likewise being biased in the first, compressed (or closed) configuration or position. The closure actuator 20 is configured to move from the first, closed position to the second, semi-compressed configuration or position, in which the closure actuator 20 is moved closer to the stationary arm 22 such that the distance d decreases but does not reach its minimum. When the closure actuator 20 is in the second, semi-compressed configuration, the jaws 16a, 16b of the end effector 14 are caused to be in the second, open position. The closure actuator 20 can then move from the second, semi-compressed configuration to the third, compressed (or closed) configuration or position, in which the actuator 20 is moved even closer to the stationary arm 22, in comparison to the second, semi-compressed configuration, and reaches its minimum possible distance d. Thus, the distance d between the closure actuator 20 and the stationary arm 22 when the closure actuator 20 is in the second, semi-compressed configuration is less than when the closure actuator 20 is in the first, uncompressed configuration, but greater than when the closure actuator 20 is in the third, compressed configuration. When the closure actuator 20 is in the third, compressed configuration, the jaws 16a, 16b of the end effector 14 can be caused to return to the first, closed position.

Whether the end effector 14 has the first profile or the second profile, the closure actuator 20 can be configured to move and thereby cause movement of the jaws 16a, 16b between positions (e.g., open and closed positions) using manual or powered components. For example, in manually actuated embodiments, the actuator 20 can be coupled to a gear that interacts with a rack extending in the handle 10 and manual movement of the actuator 20 toward the stationary arm 22 can move the rack distally toward the end effector 14, causing a force to be exerted onto the jaws 16a, 16b to, for example, open the jaws 16a, 16b. Moving the closure actuator 20 between positions may be performed by a user operating the surgical device 100 and squeezing the closure actuator 20 towards the stationary arm 22 or may be performed robotically or through some other electrical or other controlled mechanism.

Another embodiment of a surgical device 200 is shown in FIG. 4. The surgical device 200 can be configured to apply energy to tissue disposed between first and second jaws 216a, 216b via an electrode 256. The surgical device 200 is generally configured and used similar to the device 100 of FIG. 1 and includes an end effector 214 having first and second jaws 216a, 216b, an electrode 256 associated with at least one of the jaws (as shown, the first jaw 216a), a closure actuator 220, a stationary handle 222, a firing actuator 224, a force-translating component (not shown) such as a compression member), a cutting member, a proximal handle portion or housing 210, and a shaft 212 extending distally from the housing 210 and having the end effector 214 coupled to a distal end thereof. The surgical device 200 can also a motor 248, a power source 250, and a controller 254. The device 200 is configured to operatively connect to a generator 252 to provide an off-board power source for powering one or more components of the device 200, for example for powering the motor 248 and/or powering the electrode 256 as an alternate to the on-board power source 250. In the illustrated embodiment, the generator 252 is operatively coupled to the firing actuator 224. The generator 252 can be any suitable generator known in the art, such as an RF generator. The generator 252 can be a separate unit that is electrically connected to the surgical device 200 to decrease a weight and size profile of the device 200. A bore (not shown) of the shaft portion 212 can carry electrical leads or wires 230 that can deliver electrical energy to components of the end effector 214, e.g., the electrode(s) 256. The motor 248, power source 250, and controller 254 can be disposed at various locations in the device 200, such as in the proximal handle portion 210 and/or in the jaws 216a, 216b, although any one or more of the motor 248, power source 250, and controller 254 can be located off-board of the device 200.

Exemplary embodiments of devices and methods for grasping and sealing tissue are further described in U.S. Pat. Pub. No. 2015/0190191 entitled "Electrosurgical Sealing And Transecting Devices And Methods With Improved Application Of Compressive Force" filed Jan. 7, 2014, U.S. Pat. Pub. No. 2013/0161374 entitled "Layer Arrangements For Surgical Staple Cartridges" filed Feb. 8, 2013, U.S. Pat. Pub. No. 2012/0083783 entitled "Surgical Instrument With Jaw Member" filed Oct. 1, 2010, and U.S. Pat. Pub. No. 2004/0232197 entitled "Surgical Stapling Instrument Incorporating An E-Beam Firing Mechanism" filed May 20, 2003, which are incorporated by reference herein in their entireties.

Figures 5A, 5B, 5C:
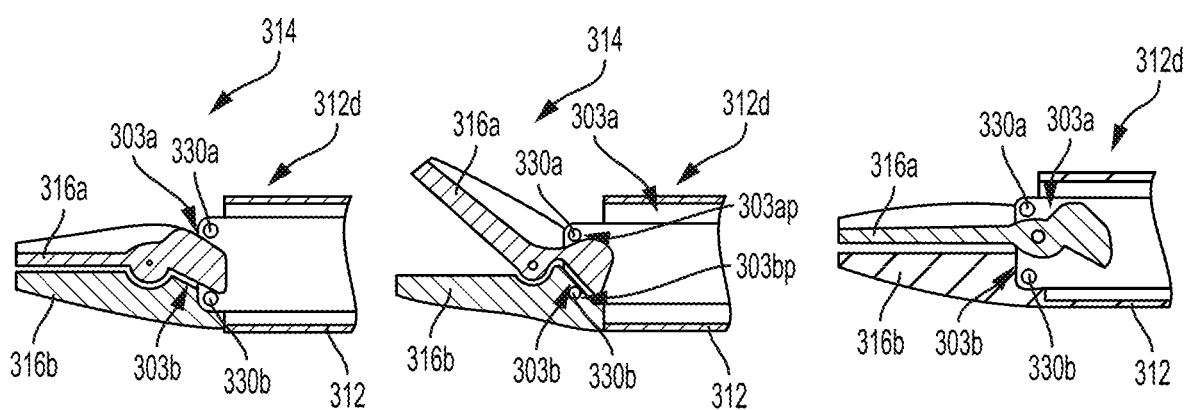
FIG. 5A is a schematic side view of one exemplary embodiment of an end effector, the end effector being in a first, biased-closed position.
FIG. 5B is a schematic side view of the end effector of FIG. 5A, the end effector being in a second, open position.
FIG. 5C is a schematic side view of the end effector of FIG. 5A, the end effector being in a third, closed position.

FIGS. 5A to 5C illustrate one embodiment of a configuration for end effectors having jaws for use in conjunction with the disclosures provided for herein, such as the end effector 14 of the device 100 of FIG. 1, as the end effector 214 of the device 200 of FIG. 4, etc. As shown in FIGS. 5A-5C, and similar to previously discussed embodiments, an end effector 314 includes jaws 316a, 316b disposed at a distal end 312d of a shaft portion 312. The jaws 316a, 316b are configured according to the second profile such that they are configured to move from a closed position (FIG. 5A) to an open position (FIG. 5B), and then from the open position back to the first, closed position (FIG. 5C). The jaws 316a, 316b are configured to move in response to actuation of a closure actuator of the surgical device that includes the end effector 14, e.g., by moving the closure actuator from a first, uncompressed configuration to a second, semi-compressed configuration and then to a third, compressed configuration. The closure actuator of the surgical device can be biased to the uncompressed configuration, for instance by a spring, to cause the jaws 316a, 316b to be biased to the first closed position (FIG. 5A).

The jaws 316a, 316b in this illustrated embodiment are configured to be moved or caused to be moved by a force-translating component as the closure actuator is actuated, such as by being squeezed towards a stationary arm of the device that includes the closure actuator. The force-translating component in this illustrate embodiment includes a rod that extends through the shaft 312 and is configured to apply compressive forces on the jaws 316a, 316b. The force-translating component is guided along recessed slots in the jaws 316a, 316b acting as a track. As the force-translating component moves distally, force is applied on one or both of the jaws 316a, 316b to approximate their inner engagement areas closer together. More specifically, upper and lower pins 330a, 330b that extend radially outward at a distal end of the force-translating component are configured to move along respective cam surfaces 303a, 303b at a proximal end of the upper jaw 316a. The force-translating component has pins 330a, 330b in this illustrated embodiment, but other configurations are possible, such as flanges. The cam surfaces 303a, 303b have a particular profile that allows for the close-open-close end effector actuation profile. Since the illustrated embodiment is a side view, similar cam surfaces formed on the other side of the jaws 316a, 316b that the pins 330a, 330b are configured to slidably engage similar to the illustrated surfaces 303a, 303b are not visible in FIGS. 5A-5C.

As shown in FIG. 5A, with the jaws 316a, 316b in the closed configuration, the pins 330a, 330b are located at a proximal end of the cam surfaces 303a, 303b, and do not exert enough force on the jaw 316a to cause the end effector 314 to open. As shown in FIG. 5B, as the force-translating component advances distally, the pins 330a, 330b advance along the respective cam surfaces 303a, 303b to an intermediate position, in turn exerting a force on the jaw 316a to cause the end effector 314 to open. The force continues to be exerted until the pins 330a, 330b reach respective pinnacles 303ap, 303bp of the cam surfaces 303a, 303b, after which the pins 330a, 330b slide down the respective cam surfaces 303a, 303b at a location distal of the intermediate position (e.g., distal of the pinnacles 303ap, 303p) as the force-translating component continues to be advanced distally. As shown in FIG. 5C, this continued distal advancement of the pins 330a, 330b distal to the pinnacles 303ap, 303bp results in the jaws 316a, 316b returning to the closed position where the pins 330a, 330b do not exert enough force on the jaw 316a to cause the end effector 314 to open.

Figure 6A:
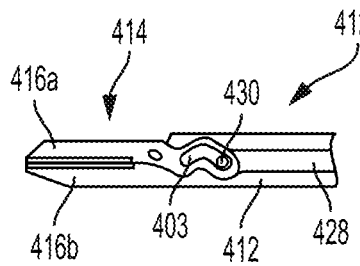
FIG. 6A is a schematic side view of another exemplary embodiment of an end effector, the end effector being in a first, biased-closed position.
Figure 6B:
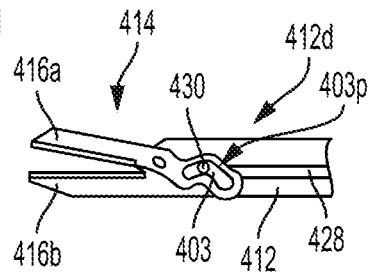
FIG. 6B is a schematic side view of the end effector of FIG. 6A, the end effector being in a second, open position.
Figure 6C:
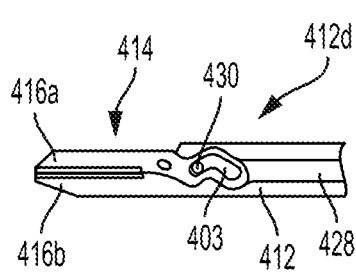
FIG. 6C is a schematic side view of the end effector of FIG. 6A, the end effector being in a third, closed position.

FIGS. 6A-6C illustrate another embodiment configuration for end effectors having jaws for use in conjunction with the disclosures provided for herein, such as the end effector 14 of the device 100 of FIG. 1, as the end effector 214 of the device 200 of FIG. 4, etc. An end effector 414 has jaws 416a, 416b, is coupled to a distal end 412d of a shaft portion 412, and is configured according to the second end effector actuation profile. The end effector 414 is configured and used similarly to the embodiment described with respect to FIGS. 5A-5C, with the cam surfaces 303a, 303b being replaced by a slot 403 formed in one of the jaws 416a. The slot 403 has a non-linear, arcuate shape such that the slot 403 has a pinnacle 403p in an intermediate portion thereof between its proximal and distal ends. The slot 403 is formed in the upper jaw 416a in this illustrated embodiment but can be formed in the lower jaw 416b, such as when the lower jaw 416b is configured to move relative to the shaft 412 to effect end effector 414 opening/closing. The slot 403 is configured to provide for the second profile of the end effector 414. Since the illustrated embodiment is a side view, a similar slot is formed on the other side of the jaws 416a, 416b that another side of a pin 430 that engages the slot 403 is configured to slidably. Additionally, the force-translating component 428 in this illustrated embodiment is in the form of a rod having distal pins, but as mentioned above, other configurations are possible.

As shown in FIG. 6A, with the jaws 416a, 416b in a closed configuration, the pin 430 is located at a proximal end of the slot 403 and does not exert enough force on the jaw 316a to cause it to open. As shown in FIG. 6B, as the force-translating component 428 advances distally, the pin 430 advances distally along the slot 403, in turn exerting a force on the jaw 416a to cause the end effector 414 to open. During this distal movement of the pin 430, the pin 430 is moving upward, e.g., in a direction away from the bottom jaw 416b. The force continues to be exerted until the pin 430 reaches the pinnacle 403p of the slot 403, at which time the end effector 414 is in the open position as shown in FIG. 6B. From the pinnacle 403p of the slot 403, the pin 403 continues to move distally along the slot 403 as the force-translating component 428 continues to be advanced distally. During this distal movement of the pin 430 distal to the pinnacle 403p, the pin 430 is moving downward, e.g., in a direction towards the bottom jaw 416b. As shown in FIG. 6C, this results in the jaws 416a, 416b returning to the closed position where the pin 430 does not exert enough force on the jaw 416a to cause the end effector 414 to open.

A person skilled in the art will understand that a variety of other cam surface and slot profiles can be used to achieve a similar result in view of the present disclosures, and thus the illustrated cam surfaces and slot profiles are in no way limiting.

Figure 7B:
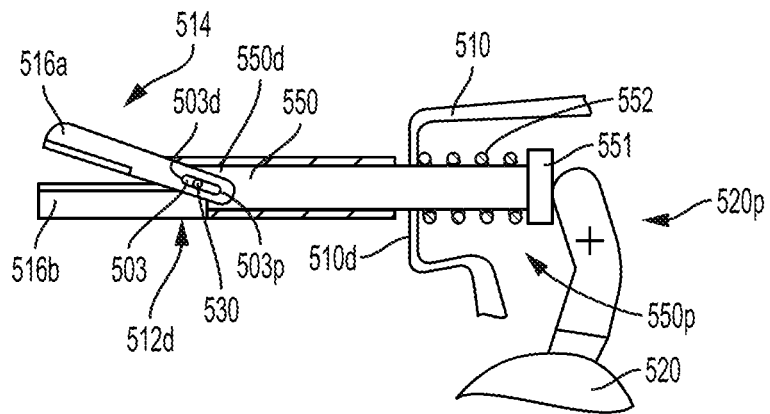
FIG. 7B is a schematic side, partial cross-sectional, semi-transparent view of a portion of the surgical device of FIG. 7A.

FIGS. 7A and 7B illustrate another embodiment of a surgical device 500. The surgical device 500 is generally configured and used similar to the device 100 of FIG. 1 and is configured to control the movement of an end effector 514 having jaws 516a, 516b disposed at a distal end 512d of a shaft portion 512. In this illustrated embodiment, a slot 503 is formed in a proximal end of one of the jaws 516a, 516b, the upper jaw 516a in this illustrated embodiment, and has a substantially linear or straight profile. A person skilled in the art will appreciate that the slot 503 may not be precisely linear or straight but nevertheless be considered to be substantially linear due to any number of factors, such as manufacturing tolerances and sensitivity of measurement devices. A pin 530p of a force-translating component in the form of a rod 550 can be disposed in the slot 503. Since the illustrated embodiment is a side view, a similar pin and slot can be present on the side not visible. The shaft portion 512 extends distally from the device's proximal handle portion or housing 510. The housing 510, which includes a closure actuator 520 and a stationary arm 522, and houses and/or engages various components, or portions thereof, for actuating the end effector 514 as discussed above. Components housed in the housing 510 for actuating the end effector 514 can define a force assembly. In other words, the components of a surgical device configured to allow the device's end effector to achieve the actuation profile of closed-open (as in the embodiment of FIGS. 7A and 7B) or the actuation profile closed-open-closed in response to actuation of the device's closure actuator can define a force assembly.

The housing 510, a portion of which is illustrated transparently in FIG. 7B, has a proximal end 550p of the rod 550 and a bias element (a spring in this illustrated embodiment) 552 disposed therein. The rod 550, which can be a pulling and/or pushing rod as in this illustrated embodiment, extends distally from a proximal end 550p in the proximal handle portion 510, through the shaft portion 512, and towards the distal end 512d of the shaft portion 512. A distal end 550d of the rod 550 includes the pin 530 extending radially outward therefrom (and a pin on the opposite side extending radially outward thereon), which is disposed in the slot 503. The rod's proximal end 550p can include a flange 551, which can be wider and/or have a larger diameter than other portions of the rod 550. The rod 550 can be connected to the spring 552 at and/or adjacent to the proximal end 550p of the rod 550. A portion of the rod 550, including the proximal end 550p, and the spring 552 can be housed within a dedicated chamber disposed within the proximal handle portion 510, or, as in this illustrated embodiment, the housing 510 can be configured to hold the rod 550 and spring 552 within its general interior while allowing for linear movement of the rod 550 proximally and distally through the shaft 512. A distal wall 510d of the housing 510 can be configured to stop the rod 550 from advancing distally beyond a certain point by engaging the portion 551 of the rod's proximal end 550p that is wider and/or of a larger diameter than the rest of the rod 550. As the proximal end 550p of the rod 550, e.g., the flange 551, engages the distal wall 510d of the housing 510, the spring 552 compresses therebetween. That is, the rod 550 is biased by the spring 552 such that the rod 550 is biased to the retracted (proximal) position when the closure actuator 520 is in an uncompressed (or open) configuration or position. When the rod 550 is in the retracted position, the pin 530 is disposed at a proximal end 503*p* of the slot 503, which applies a force to the jaw 516*a* to maintain the end effector 514 in the closed position.

The closure actuator 520 can include a portion 520*p* disposed within the housing 510 and configured to engage the flange 551 of the rod 550. The portion 520*p* is in the form of a lever or finger in this illustrated embodiment. As the closure actuator 520 is advanced from the uncompressed configuration and towards the compressed (or closed) configuration or position by applying pressure to the closure actuator 520 in a direction substantially in the direction of the stationary arm 522, the portion 520*p* of the closure actuator 520 is moved distally towards the distal end 512*d* of the shaft 512 such that the portion 520*p* presses, pushes and/or applies force against the flange 551 distally. This distal force applied by the closure actuator 520 to the rod 550 causes the spring 552 to compress against the housing's distal wall 510*d* as the rod 550 is distally advanced through the shaft portion 512, the distal advancement of the rod 550 causes the pin 530 to slide distally within the slot 503 towards a distal end 503*d* of the slot 503, thereby causing the upper jaw 516*a* to pivot away from the lower jaw 516*b*, thus moving the end effector 514 from a first, closed position, toward a second, open position. FIG. 7B shows the end effector 514 in a semi-open position between the closed and open positions. When the pin 503 reaches the distal end 503*d* of the slot 503, the end effector 514 is in the open position. FIG. 7A shows the end effector 514 in the open position.

In another embodiment, the embodiment illustrated in FIGS. 7A and 7B can be modified so that the rod 550 is pulled proximally to move the jaws 516*a*, 516 from the closed position to the open position, with the pin 530 starting at the slot's distal end 503*d* and moving proximally to the slot's proximal end 503*p*.

Figure 8:
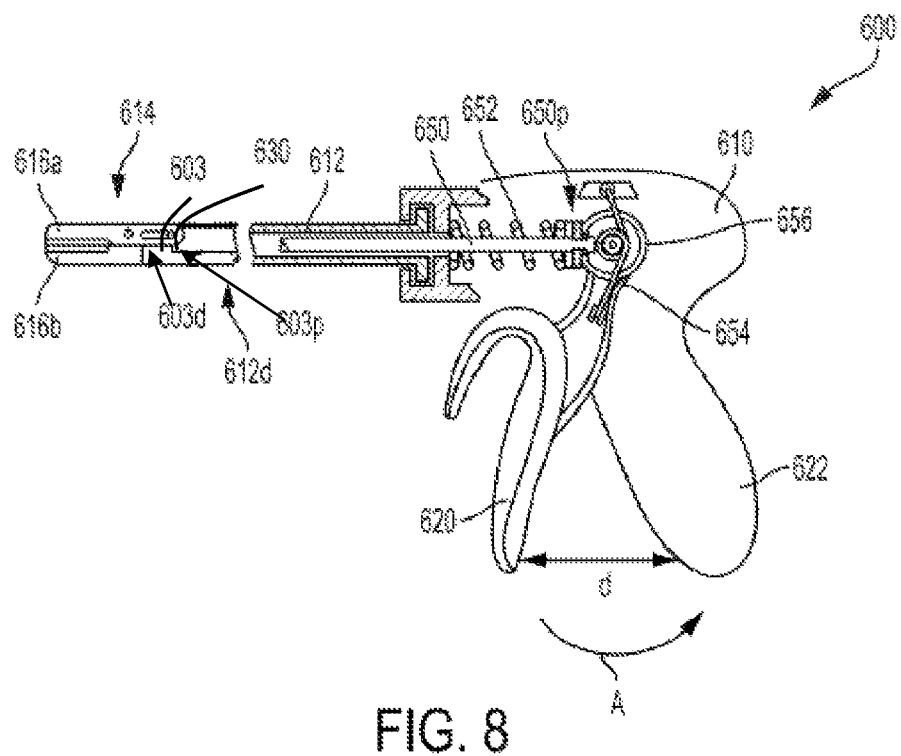
FIG. 8 is a schematic side, partial cross-sectional, semi-transparent view of still another exemplary embodiment of a surgical device, the device having an end effector and a housing with an actuator, a stationary arm, a torsion spring, a compression spring, and an internal cam mechanism.
Figure 9A:
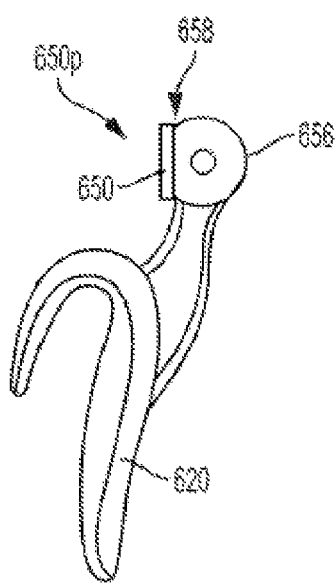
FIG. 9A is a side view of the actuator and the internal cam mechanism of FIG. 8, the actuator being in a first, uncompressed configuration in which it is spaced apart from the stationary arm (not shown)
Figure 9B:
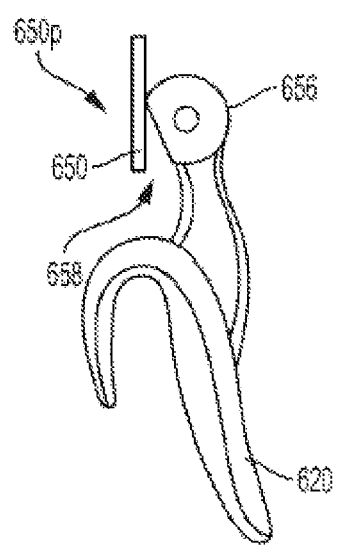
FIG. 9B is a side view of the actuator and the internal cam mechanism of FIG. 9A, the actuator being in a second, compressed configuration in which it is closed to the stationary arm (not shown)

FIGS. 8-9B illustrate another embodiment of a surgical device 600. The surgical device 600 is generally configured and used similar to the device 100 of FIG. 1 and is configured to control the movement of an end effector 614 having jaws 616*a*, 616*b* disposed at a distal end 612*d* of a shaft portion 612. In this illustrated embodiment, a slot 603 is formed in a proximal end of one of the jaws 616*a*, 616*b* (the upper jaw 616*a* in this illustrated embodiment) and has a substantially linear or straight profile. A pin 630 of a force-translating component in the form of a rod 650 can be disposed in the slot 603. Since the illustrated embodiment is a side view, a similar pin and slot can be present on the side not visible. The shaft portion extends distally from the device's proximal handle portion or housing 610, which includes a closure actuator 620 and a stationary arm 622, and houses and/or engages various components, or portions thereof, for actuating the end effector 514 as discussed above.

The housing 610, which is illustrated transparently in FIG. 8, has a bias element 654 in the form of a torsion spring coupled to the closure actuator 620 and to the housing 610. The bias element 654 is configured to provide a bias to the closure actuator 620 to force the actuator 620 to an uncompressed (or open) configuration or position. The closure actuator 620 includes and/or is connected to a cam 656 configured to engage the rod 650 to selectively apply or release pressure thereon such that the rod 650 is selectively distally extended or proximally retracted through the shaft portion 612, respectively, towards and away from the distal end of the shaft 612*d*. As shown in FIGS. 9A and 9B, the cam 656 has a profile that includes a flat portion that defines a cam surface 658 and that faces the proximal end 650*p* of the rod 650. The cam surface 658 has different positions relative to the rod 650, e.g., the proximal end 650*p* thereof, depending on whether the closure actuator 620 is in the compressed position (FIG. 9B) or the uncompressed configuration (FIGS. 8 and 9A), wand the cam 656 also has a non-flat portion (e.g., rounded or elliptical, among other shapes). When the closure actuator 620 is moved from the uncompressed configuration towards the compressed configuration, the rod 650 is pushed distally and the cam 656 rotates such that the flat portion 658 moves out of engagement with the flat proximal-facing surface at the proximal end 650*p* of the rod 650 and the cam's non-flat portion engages the flat proximal-facing surface at the proximal end 650*p* of the rod 650.

When the closure actuator 620 is in the first, uncompressed configuration, the rod 650 is in the retracted position in a direction away from the distal end 612*d* of the shaft 612, and the jaws 616*a*, 616*b* are in the first, closed position with the pin 630 disposed at a proximal end 603*p* of the slot 603, as shown in FIG. 8. When the closure actuator 620 is in the first, uncompressed configuration, the cam surface 658 can be in contact with the proximal end 650*p* of the rod 650 such that no force, or at least an amount of force that is not enough to displace the rod 650 in a distal direction, is being applied by the cam 656 or cam surface 658 on the rod 650. Thus, any contact between the cam surface 658 and the rod 650 is insufficient to cause the rod 650 to move distally and change the position of the pin 630 in the slot 603, and thus is insufficient to open the jaws 616*a*, 616*b*.

When the closure actuator 620 is moved from the first, compressed configuration to the second, compressed (or closed) configuration or position, the cam 656 rotates as shown in FIG. 9B. Rotating the cam 656 causes at least a portion of the cam 658 to remain in contact with the rod 650 as the cam 656 moves or pivots relative to the proximal end 650*p* of the rod 650 in the direction of the rod 650 towards the distal end 612*d*. The pushing and/or pressuring of the rod 650 by the cam 656 is performed with sufficient force to cause the spring 652 to be compressed. The rod's distal movement also causes the pin 630 to advance towards the distal end 603*d* of the slot 603, thus causing the upper jaw 616*a* to pivot away from the lower jaw 616*b* such the end effector 614 moves toward the second, open position. When the pin 630 reaches the distal end of the slot 603, the end effector 614 is in the open position. In at least some embodiments, once the jaws 616*a*, 616*b* are in the second, open position, force from the spring 652 can act upon the cam 656 in a direction normal to the cam's pivot axis, thereby allowing the closure actuator 620 to remain in the second, compressed configuration with minimal force applied thereto, e.g., with minimal force needed from a user actuating the closure actuator 620.

FIGS. 10A-11C illustrate another embodiment of the jaws 616*a*, 616*b* of the device 600 in which the end effector 614 is configured to move in the second profile (closed-open-closed). The device 600 in this illustrated embodiment includes a cam 656' having a cam surface 658', which are similar to the cam 656 and cam surface 658 of the embodiment of FIGS. 8-9B except that the cam 656' and cam surface 658' are configured to allow for the closed-open-closed end effector articulation profile. The device 600 in this illustrated embodiment includes a rod 650', which is similar to the rod 650 of the embodiment of FIGS. 8-9B except that the rod 650's proximal end 650*p* that engages the cam surface 658' is not a flat surface. Instead, the rod's proximal end 650p includes an engagement feature configured to engage the cam 656', e.g., the cam surface 658' thereof, to allow for the closed-open-closed end effector articulation profile. The position of the jaws 616a, 616b shown in FIGS. 10A, 10B, and 10C correspond, respectively, to the position of the closure actuator 620 in FIGS. 11A, 11B, and 11C. More specifically, in FIGS. 10A, 10B, and 10C, the jaws 616a, 616b are illustrated in a closed position, open position, and closed position, respectively, while in each of FIGS. 11A, 11B, and 11C, the closure actuator 620 is illustrated in an uncompressed (or open) configuration, semi-compressed configuration, and compressed (or closed) configuration, respectively.

As shown in FIGS. 11A-11C, the closure actuator 620 includes and/or is connected to the cam 656' and the cam surface 658'. The cam surface 658' is configured to interact with the proximal end 650p' of the rod 650' similar to that discussed above regarding the rod 650 and cam surface 658 of FIGS. 8-9B. The cam surface 658' includes lower and upper concave portions 658c', 658d' and an extended portion 658e' disposed therebetween. This configuration of the cam surface 658' in which the cam 656' has three surface portions configured to sequentially engage the rod 650' enables the closure actuator 620 to be moved to three different positions or configurations: the uncompressed or open configuration or position, the semi-compressed or semi-open/closed configuration or position, and the compressed or closed configuration or position. Accordingly, the jaws 616a, 616b are configured to be moved from the closed position to the open position, and from the open position back to the closed position.

The closure actuator 620 is biased to the uncompressed configuration using a bias element 654, which is in the form of a torsion spring 654 in this illustrated embodiment. When the closure actuator 620 is in the uncompressed configuration, the closure actuator is positioned at a maximum distance from the stationary arm 622, and the lower convex portion 658c' of the cam surface 658' is in contact with the engagement feature at the proximal end 650p' of the rod 650' such that the rod 650' (e.g., the engagement feature thereof) is seated in the lower convex portion 658c' of the cam surface 658', and the rod 650' is maintained in its initial biased position at a maximum distance from a distal end 612d of the shaft 612. In other words, the proximal end 650p' of the rod 650' being seated in the lower convex portion 658' prevents the rod's movement when no pressure, or pressure less than a predetermined threshold amount, is applied to the closure actuator 620. This positioning of the closure actuator 620, cam 656', cam surface 658', lower concave portion 658c', and rod 650', as shown in FIG. 11A, causes the jaws 616a, 616b to be and/or remain in the closed position, as shown in FIG. 10A. As shown in FIG. 10A, the pin 630 is disposed in the proximal end 603p of the slot 603 when the end effector 614 is in the closed position and the closure actuator 620 is in the uncompressed position.

When the closure actuator 620 is moved to the second, semi-compressed configuration, the cam 656' and cam surface 658' rotates or pivots such that the extension 658e' contacts with the proximal end 650p' of the rod 650' (e.g., with the rod's the engagement feature), as shown in FIG. 11B. Such contact between the extension 658e' and the rod 650' causes the rod 650' to advance or move distally through the shaft 612 towards the distal end 612d and the pin 630 to slide distally in the slot 603. This movement of the rod 650' causes the jaws 616a, 616b to move from the closed position to the open position, as shown in FIG. 10B. In the open position, the pin 630 is disposed in the distal end 603d of the slot 603. The closure actuator 620 is closer to the stationary arm in the second, semi-compressed configuration, e.g., as shown in FIG. 11B, than when the closure actuator 620 is in the first, uncompressed configuration, e.g., as shown in FIG. 11A.

The closure actuator 620 is configured to be moved from the second, semi-compressed configuration to the third, compressed configuration. In the third, compressed configuration, the closure actuator 620 is at a minimum distance from the stationary arm 622. When the closure actuator 620 is moved to the third, compressed configuration, the cam 656' and the cam surface 658' rotate or pivot such that the proximal end 650p' of the rod 650' (e.g., the engagement feature thereof) is seated in the upper concave portion 658d' of the cam 656'. In other words, the proximal end 650p' of the rod 650' being seated in the upper convex portion 658' prevents the rod's movement when no pressure, or pressure less than a predetermined threshold amount, is applied to the closure actuator 620. Moreover, such positioning of the cam 656', cam surface 658', and its concave portion 658e' causes the rod 650' to retract towards the proximal end of the housing 610 and away from the distal end 612d of the shaft 612. This movement or retraction of the rod 650' causes the jaws 616a, 616b to move from the open position to the closed position, as shown in FIG. 10C. The pin 630 is disposed in the proximal end 603p of the slot 603 when the end effector 614 is in the closed position and the closure actuator 620 is in the compressed position. The closure actuator 620 is closer to the stationary arm in the third, compressed configuration, e.g., as shown in FIG. 11C, than when the closure actuator 620 is in the second, semi-compressed configuration, e.g., as shown in FIG. 11B.

The closure actuator 620 can be moved away from the stationary arm 622 manually by applying a pushing force on the actuator 620, or can be moved away from the station arm 622 automatically by way of the tension spring 654 in the handle that biases the closure actuator 620 to the closed position.

Figure 12:
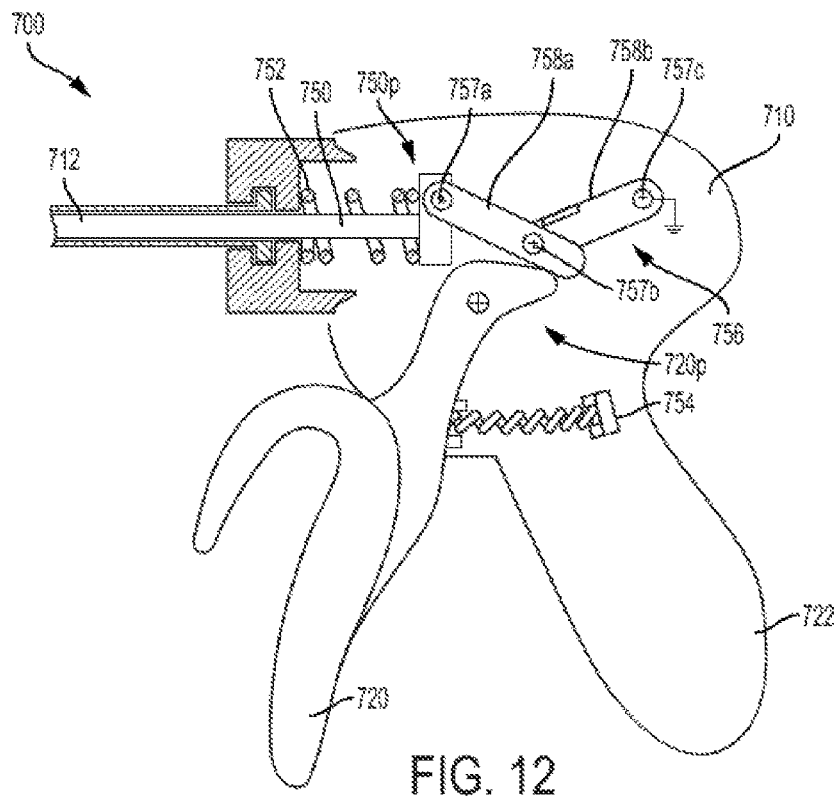
FIG. 12 is a schematic side, partial cross-sectional, semi-transparent view of another exemplary embodiment of a surgical device, the device having an end effector (not shown) and a housing with an actuator, a stationary arm, a compression spring, and internal linkages, the compression spring and the internal linkages being configured to bias an internal shaft distally when the actuator is in a first, uncompressed configuration, which in turn causes the end effector to be in a first, closed position.

FIG. 12 illustrates another embodiment of a surgical device 700. The surgical device 700 is generally configured and used similar to the device 100 of FIG. 1 and includes a proximal handle portion or housing 710, a closure actuator 720, and a stationary arm 722, among other components. In this illustrated embodiment, a rod 750 is configured to move within a shaft 712 that extends distally from the housing 710, and the shaft 712 includes an end effector (not shown) having jaws (not shown) coupled to a distal end (not shown) of the shaft 712. The end effector can be configured with the first profile (closed-open) or the second profile (closed-open-closed)

A proximal end 750p of the rod 750 located within the proximal handle portion 710 is coupled to a linkage assembly 756 disposed in the proximal handle portion 710. The linkage 756 assembly includes two bars 758a, 758b. The first bar 758 a is attached to the proximal end 750p of the rod 750 at a first pivot point 757a. The first bar 758a and second bar 758b are attached to one another at a second pivot point 757b. The second bar 758b is attached to the housing 710 at a third pivot point 757c. Each of the pivot points 757a, 757b, 757c is configured such that the bars 758a, 758b are configured to rotate about the pivot points to which they are respectively attached. The linkage assembly 756 in other embodiments can include another number of bars and attachment points, depending on the desired configuration.

The surgical device 700 also includes a bias element 754 in the form of a spring. At its distal end the spring 754 engages the closure actuator 720. At its proximal end the spring 754 engages the stationary arm 722 or the housing 710. The spring 754 provides a bias such that the closure actuator 720 is biased to the uncompressed or open configuration, which is shown in FIG. 12. As the closure actuator 720 is advanced towards the stationary arm 722, the spring 754 compresses and, when the closure actuator 720 is released, the spring 754 biases the closure actuator 720 back to its uncompressed configuration.

The housing 710, which is illustrated transparently in FIG. 12, houses a proximal portion 720p of the closure actuator 720 that is coupled with the linkage assembly 756. When the closure actuator 720 is in the uncompressed configuration, the closure actuator 720 applies an amount of force, which can be a zero force, on the linkage assembly 756 such that the bars 758a, 758b are in a first configuration. In the first configuration the bars 758a, 758b can be angularly oriented relative to one another at a non-zero angle, as in this illustrated embodiment. As the closure actuator 720 is moved from the uncompressed configuration, towards the compressed configuration, the proximal portion 720p of the closure actuator 720 applies force to the linkage assembly 756, thereby causing the bars 758a, 758b to move such that the bars 758a, 758b pivot at their respective ones of the pivot points 757a, 757b, 757c to move from the first configuration to a second configuration. In the second configuration, the bars 758a, 758b can be nearly substantially longitudinally aligned, e.g., nearly form a substantially straight or zero angle therebetween, as in this illustrated embodiment. The bars 758a, 758b being close to, but not quite, being substantially longitudinally aligned in the second configuration may help prevent the bars 758a, 758b from locking in the second configuration to facilitate movement thereof back to the first configuration. The movement of the bars 758a, 758b from the first configuration to the second configuration causes the proximal end 750p of the rod 750 to receive force or pressure from the first bar 757a in a direction towards the distal end of the shaft 712. FIG. 12 shows the bars 758a, 758b in the second configuration in which the bars 758a, 758b are at a non-zero angle relative to one another. As the rod 750 is advanced distally in response to actuation of the closure actuator 720, a second bias element in the form of a spring 752 compresses and the jaws of the surgical device are caused to move from a closed position to an open position. The closure actuator 720 may be moved from the open position to the closed position by the force of the compressed springs 752 and/or 754 that bias the closure actuator 720 away from the stationary arm 722. In at least some embodiments, the closure actuator 720 can be moved from its compressed configuration to its uncompressed configuration by applying pressure to the closure actuator 720 in a direction away from stationary arm 722.

Figure 13A:
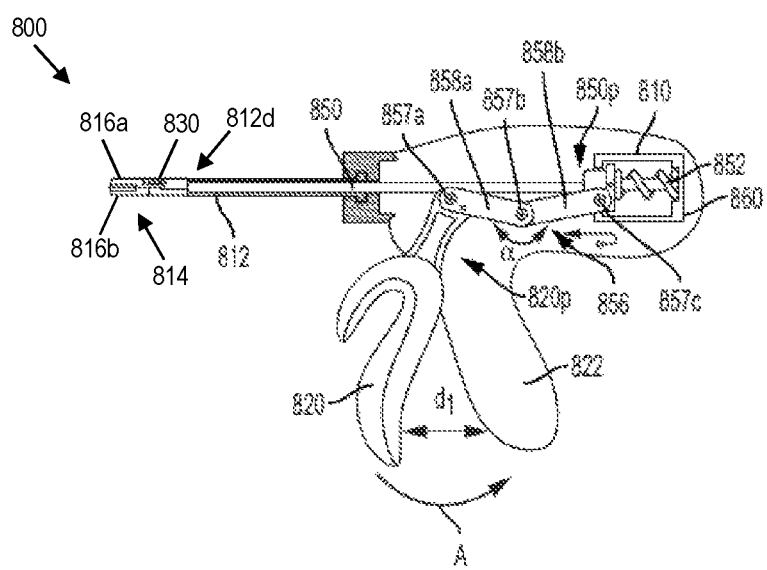
FIG. 13A is schematic side, partial cross-sectional, semi-transparent view of still another exemplary embodiment of a surgical device, the device having an end effector and a housing with an actuator, a stationary arm, a spring, and internal linkages, the internal linkages being in a first, angled position, the actuator is in a first, uncompressed configuration, and the end effector is in a first, closed position.
Figure 13B:
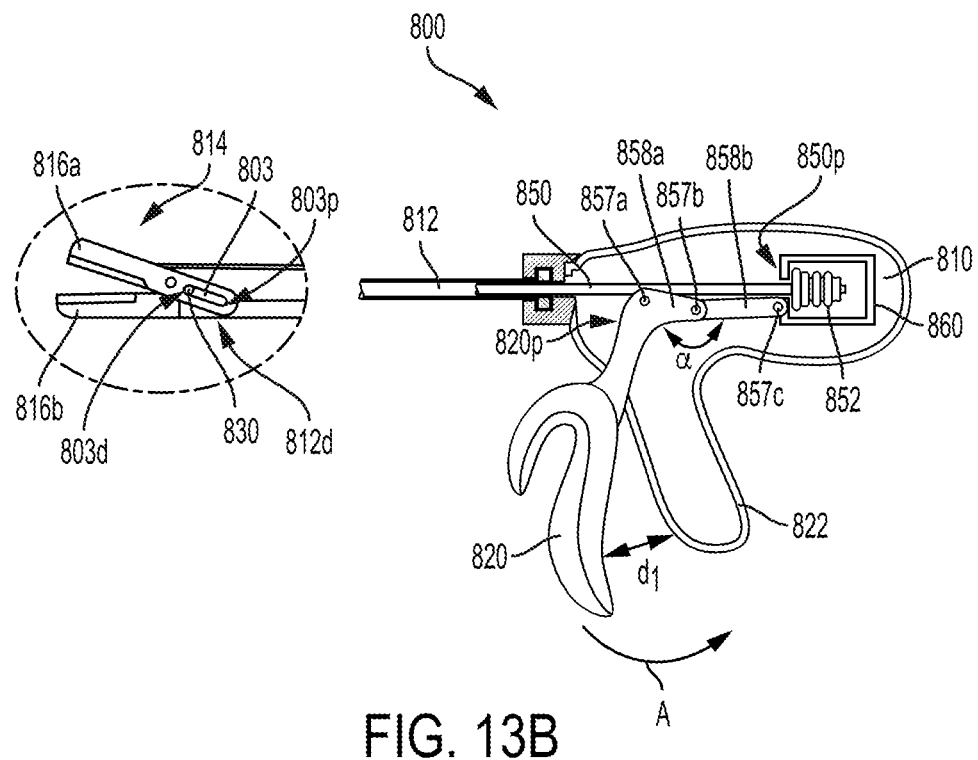
FIG. 13B is a schematic side, partial cross-sectional, semi-transparent view of the device of FIG. 13A in which the internal linkages are in a second, extended position, the actuator is in a second, semi-compressed configuration, and the end effector is in a second, open position.
Figure 13C:
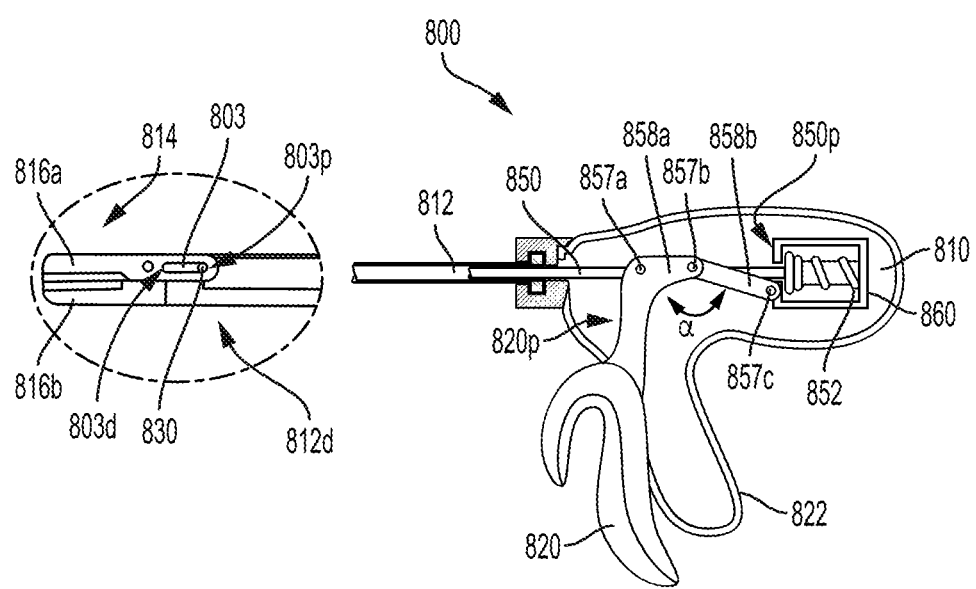
FIG. 13C is a schematic side, partial cross-sectional, semi-transparent view of the device of FIG. 13B in which the internal linkages are in a third, angled position, the actuator is in a third, compressed configuration, and the end effector is in a third, closed position.

FIGS. 13A-13C illustrate another embodiment of a surgical device 800. The surgical device 800 is generally configured and used similar to the device 100 of FIG. 1 and includes a proximal handle portion 810, a closure actuator 820, a stationary arm 822, a rod 850 configured to move through a shaft 812 extending distally from the proximal handle portion 810, and an end effector 814 having jaws 816a, 816b. The upper jaw 816a has formed therein a slot 803 having proximal and distal ends 803p, 803d. A pin 830 at a distal end of the rod 850 is disposed in the slot 803. Since the illustrated embodiment is a side view, a similar pin and slot can be present on the side not visible.

The proximal handle portion 810, which is illustrated transparently in FIGS. 13A-13C, houses a proximal end 850p of the rod 850 that is coupled to a linkage assembly 856 that includes first and second bars 858a, 858b. The first bar 858a is attached to the rod 850 at a first pivot point 857a between the distal end 850d and proximal end 850p of the rod 850. The first bar 858a is also attached to the closure actuator 820 at the first pivot point 857a. The first bar 858a and the second bar 858b are attached to one another at a second pivot point 857b. The second bar 858b is attached to a proximal end 850p of the rod 850 at a third pivot point 857c. Each of the pivot points 857a, 857b, 857c is configured such that the bars 858a, 858b are configured to rotate about the pivot points to which they are respectively attached. The linkage assembly 856 in other embodiments can include another number of bars and attachment points, depending on the desired configuration.

The proximal end 850p of the rod 850 engages a bias element in the form of a spring 852. The spring 852 and the proximal end of the rod 850 are disposed in a chamber 860 located in the housing 810. The chamber 860 is configured to control the range and points of compression of the spring 852. When the closure actuator 820 is in an uncompressed or open configuration or position, the rod 850 is retracted away from a distal end 812d of the shaft 812, thereby causing the spring 852 to be uncompressed within the chamber 860. The spring 852 is thus configured to bias the rod 850 to a retracted position and the closure actuator 820 to the uncompressed configuration, as shown in FIG. 13A. When the closure actuator 820 is in the uncompressed configuration, the linkage assembly 856 is in a retracted configuration in which the bars 858a, 858b form a non-zero angle α relative to one another. The angle α formed by the bars 858a, 858b when the closure actuator 820 is in the compressed configuration can be greater than 180°, as in this illustrated embodiment. When the rod 850 is in the retracted position, the jaws 816a, 816b are in a closed position, as shown in FIG. 13A. In the closed position, the pin 830 is located at the proximal end 803p of the slot 803.

As the closure actuator 820 is moved from the compressed configuration to a semi-compressed configuration by moving closer to the stationary arm 822, the bars 858a, 858b pivot at their respective ones of the pivot points 857a, 857b, 857c to move from the non-zero angle α towards an intermediate position in which the bars 858a, 858b are at a smaller angle α, as shown in FIG. 13B. In some embodiments, the smaller angle α can have a non-zero value, while in other embodiments, the smaller angle α can be substantially zero. A person skilled in the art will appreciate that a value may not be precisely at a value but nevertheless be considered to be at about that value due to any one or more factors, such as manufacturing tolerances and sensitivity of measurement devices. As the bars 858a, 858b move towards the intermediate position, the rod 850 is advances towards the distal end 812d of the shaft 812 and the spring 852 compresses against inner walls of the chamber 860 proximal to the rod 850, as shown in FIG. 13B. When the rod 850 is advanced to an extended position, the jaws 816a, 816b are forced to move from a closed position to an open position. In the open position, the pin 830 is in the distal end 803d of the slot 803. In the semi-compressed configuration (FIG. 13B), the distance d1 between the closure actuator 820 and the stationary arm 822 is less than the distance d1 therebetween when the closure actuator 820 is in the uncompressed configuration (FIG. 13A) and is greater than the distance d1 therebetween when the closure actuator 820 is in the compressed configuration (FIG. 13C).

As the closure actuator 820 is moved from the semi-compressed configuration to the compressed configuration by moving closer to the stationary arm 822 such that the actuator 820 and the arm 822 are in contact or substantially adjacent with one another, the bars 858*a*, 858*b* move from the intermediate position to a second non-zero angular position, the second bent position being opposed to the first non-zero angular position of the bars 858*a*, 858*b* when the closure actuator 820 is in the uncompressed configuration. As shown in FIG. 13C, the angle α when the closure actuator 820 is in the compressed configuration is less than 180°, e.g., the angle α in FIG. 13C is less than about 180° by about the same amount that the angle α in FIG. 13A is greater than about 180°. In at least some embodiments, when the closure actuator 820 is moved to a compressed configuration, the second pivot point 857*b* is moved distally from the closure actuator 820 and/or stationary arm 822. As the bars 858*a*, 858*b* move in response to the closure actuator 820 moving from the semi-compressed configuration to the compressed configuration, the rod 850 retracts and/or is driven away from the distal end 812*d* of the shaft 812, allowing the spring 852 to return to its uncompressed state, as shown in FIG. 13C. As the rod 850 retracts and/or is driven away from the distal end 812*d* of the shaft, the jaws 816*a*, 816*b* return to the closed position, as also shown in FIG. 13C. In the closed position, the pin 830 is at the proximal end 803*p* of the slot 803.

If the closure actuator 820 is released and/or the force applied on the closure actuator 820 towards the stationary arms 822 drops below a predetermined threshold force, the spring 852 naturally returns to its uncompressed state, as shown in FIG. 13A. When the spring 852 is returned to its biased uncompressed state, the bars 858*a*, 858*b* return to their biased, angled position, thereby allowing the rod 850 to retract and the closure actuator 820 to move back to its open position.

In embodiments in which the end effector is described as including a slot therein configured to have a force-translating component disposed therein, e.g., a pin or flange of the force-translating component, the force-translating component can instead include the slot and the end effector can instead include the feature (e.g., a pin, flange, etc.) that is disposed in the slot.

A person skilled in the art will appreciate that the present invention has application in conventional endoscopic and open surgical instrumentation as well application in robotic-assisted surgery. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and its contents are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that device is sterilized. This can be done by any number of ways known to those skilled in the art including beta or gamma radiation, ethylene oxide, and/or steam.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
an elongate shaft having at a distal end thereof jaws configured to engage tissue and to move between open and closed positions, the jaws being biased to the closed position;
an elongate rod extending along the shaft and operatively coupled to the jaws; and
an actuator operatively coupled to the rod and configured to be actuated to move from a first position, in which the jaws are in the closed position, to a second position and thereby cause the rod to move distally, the distal movement of the rod being configured to cause the jaws to move from the closed position towards the open position, wherein the actuator is configured to move from the second position to a third position and thereby continue moving the rod distally, the continued distal movement of the rod being configured to cause the jaws to move from the open position back to the closed position.

2. The device of claim 1, wherein the closure actuator includes a movable trigger.

* * * * *